(12) United States Patent
Huang et al.

(10) Patent No.: US 7,303,881 B2
(45) Date of Patent: Dec. 4, 2007

(54) ANTIGEN DELIVERY COMPOSITIONS AND METHODS OF USE

(75) Inventors: Leaf Huang, Pittsburgh, PA (US); Zhengrong Cui, Corvallis, OR (US); John Dileo, Stafford, VA (US); Su-Ji Han, Gwangju (KR); Dileep P. Vangasseri, Thrissur (IN)

(73) Assignee: PDS Biotechnology Corporation, Liberty Township, OH (US)

( * ) Notice: Subject to any disclaimer, the term of this patent is extended or adjusted under 35 U.S.C. 154(b) by 283 days.

(21) Appl. No.: 11/121,840

(22) Filed: May 2, 2005

(65) Prior Publication Data

US 2006/0008472 A1 Jan. 12, 2006

Related U.S. Application Data

(60) Provisional application No. 60/567,291, filed on Apr. 30, 2004.

(51) Int. Cl.
*C12Q 1/68* (2006.01)
(52) U.S. Cl. .......................................... 435/6; 977/907
(58) Field of Classification Search ................ 435/6, 435/69.1; 977/907
See application file for complete search history.

(56) References Cited

U.S. PATENT DOCUMENTS

| | | | |
|---|---|---|---|
| 5,264,618 | A | 11/1993 | Felgner et al. |
| 5,334,761 | A | 8/1994 | Gebeyehu et al. |
| 5,459,127 | A | 10/1995 | Felgner et al. |
| 6,008,202 | A | 12/1999 | Huang et al. |
| 6,586,409 | B1 | 7/2003 | Wheeler |
| 6,649,170 | B1 | 11/2003 | Lindblad et al. |
| 6,693,086 | B1 | 2/2004 | Dow et al. |
| 6,710,035 | B2 | 3/2004 | Felgner et al. |
| 6,780,421 | B1 | 8/2004 | Haensler et al. |
| 7,001,614 | B2 | 2/2006 | Smyth-Templeton et al. |
| 7,105,574 | B1 | 9/2006 | Wheeler |
| 2003/0008813 | A1 | 1/2003 | Felgner et al. |
| 2005/0245446 | A1 | 11/2005 | Hailes et al. |
| 2006/0051405 | A1 | 3/2006 | MacLachlan et al. |
| 2006/0083780 | A1 | 4/2006 | Heyes et al. |
| 2006/0165708 | A1 | 7/2006 | Mayumi et al. |
| 2006/0182793 | A1 | 8/2006 | Bachmann et al. |
| 2006/0204566 | A1 | 9/2006 | Smyth-Templeton et al. |
| 2006/0223769 | A1 | 10/2006 | Dow et al. |
| 2006/0275777 | A1 | 12/2006 | Waelti |
| 2007/0059318 | A1 | 3/2007 | Balu-Iyer et al. |

FOREIGN PATENT DOCUMENTS

WO 03095641 A1 11/2003

OTHER PUBLICATIONS

Steller et al. Clinical Cancer Research, 1998, vol. 4, pp. 2103-2109.*
Dileo, et al., "Lipid-Protamine-DNA-Medicated Antigen Delivery to Antigen-Presenting Cells Results in Enhanced Anti-tumor Immune Responses", Molecular Therapy, vol. 7, No. 5, (May 2003) pp. 640-648.
Cui, et al., "Immunostimulation Mechanism of LPD Nanoparticle as a Vaccine Carrier", Molecular Pharmaceutics, vol. 2, No. 1, (Dec. 14, 2004) pp. 22-28.
Chen and Huang, "Cationic Liposome-based Peptide Vaccine: Potent Therapeutics for Cervical Cancer", Poster, May 20, 2006.
Brunel, et al., Cationic Lipid DC-Chol Induces an Improved and Balanced Immunity Able to Overcome the Unresponsiveness to the Hepatitis B Vaccine, Vaccine, Apr. 1999, 2192-2203, vol. 17.
Walker, et al., Cationic Lipids Direct a Viral Glycoprotein into the Class I Major Histocompatibility Complex Antigen-Presentation Pathway, Proc. Natl. Acad. Sci. USA, Sep. 1992, 7915-7918, vol. 89.
Joseph, et al., A New Intranasal Influenza Vaccine Based on a Novel Polycationic Lipid-Ceramide Carbamoyl-Spermine (CCS) I. Immunogenicity and Efficacy Studies in Mice, Vaccine, 2006, 3990-4006, vol. 24.
Jiao, et al., Modulation of Cellular Immune Response Against Hepatitis C Virus Nonstructural Protein 3 by Cationic Liposome Encapsulated DNA Immunization, Hepatology, Feb. 2003, 452-460. vol. 37, No. 2.
Yasuda, et al., Endosomal Translocation of Vertebrate DNA Activates Dendritic Cells via TLR9-Dependant and Independent Pathways, The Journal of Immunology, 2005, 6129-6136, vol. 174.
Holten-Andersen, et al., Combination of the Cationic Surfactant Dimethyl Dioctadecyl Ammonium Bromide and Synthetic Mycobacterial Cord Factor as an Efficient Adjuvant for Tuberculosis Subunit Vaccines, Infection and Immunity, Mar. 2004, 1608-1617, vol. 72, No. 3.
Sprott, et al., Activation of Dentritic Cells by Liposomes Prepared from Phosphatidylinositol Mannosides from Mycobacterium Bovis Bacillus Calmette-Guerin and Adjuvant Activity In Vivo, Infection and Immunity, Sep. 2004, 5235-5246, vol. 72, No. 9.
Zaks, et al., Efficient Immunization and Cross-Priming by Vaccine Adjuvants Containing TLR3 or TLR9 Agonists Complexed to Cationic Liposomes, The Journal of Immunology, 2006, 7335-7345, vol. 176.
Korsholm, Unravelling the Adjuvant Mechanism of Cationic Liposomes, Statens Serum Institut, Jun. 2006, 15.00-15.30.
Rughetti, et al., Transfected Human Dendritic Cells to Induce Antitumor Immunity, Sep. 2000, 1458-1466, vol. 7, No. 17.
Cui, et al., Coating of Mannan on LPD Particles Containing HPV E7 Peptide Significantly Enhances Immunity Against HPV-Positive Tumor, Jun. 2004, 1018-1025, vol. 21, No. 6.

* cited by examiner

*Primary Examiner*—Ali R. Salimi
(74) *Attorney, Agent, or Firm*—Wood, Herron & Evans, L.L.P.

(57) ABSTRACT

The present invention provides antigen delivery compositions and methods of using same to prevent or to treat cancers and other infectious diseases.

5 Claims, 21 Drawing Sheets

12h

24h

48h

ANTIGEN DELIVERY COMPOSITIONS AND METHODS OF USE

CROSS-REFERENCES TO RELATED APPLICATIONS

This application claims benefit of U.S. Provisional Application No. 60/567,291, filed Apr. 30, 2004, which application is incorporated herein by reference for all purposes.

BACKGROUND OF THE INVENTION

To prevent and treat many of the deadly diseases and cancers, effective vaccines are needed. The new generation vaccine has many advantages over traditional vaccine. However, the potency of the new generation vaccine needs to be enhanced. Unfortunately, after 80 some years of development, Alum is still the only single adjuvant approved by the Food and Drug Administration (FDA) in the United States for use in humans. Therefore, novel vaccine delivery systems and/or adjuvants are desperately needed and desired.

SUMMARY OF THE INVENTION

The present invention provides antigen delivery compositions/adjuvants and methods of using same to prevent or to treat cancers and other infectious diseases. More particularly, the present invention provides a lipid-protamine-DNA (LPD) vaccine delivery system/adjuvant and methods of using such LPD vaccine delivery system/adjuvant for the prevention and treatment of cancer and other infectious diseases. In fact, it has surprisingly been found that the LPD vaccines of the present invention can induce strong cellular immunity to cause complete regression of established tumors and to prevent the formation of new tumors.

LPD) were injected with TC-1 cells (5×10⁵/mouse) on day 0. On day 4 and 10, they were treated with E7 in different formulations. Tumor sizes were reported as a function of time. Statistical analysis showed that the values for E7m/LPD and E7/LPD are not different.

Figure 16:
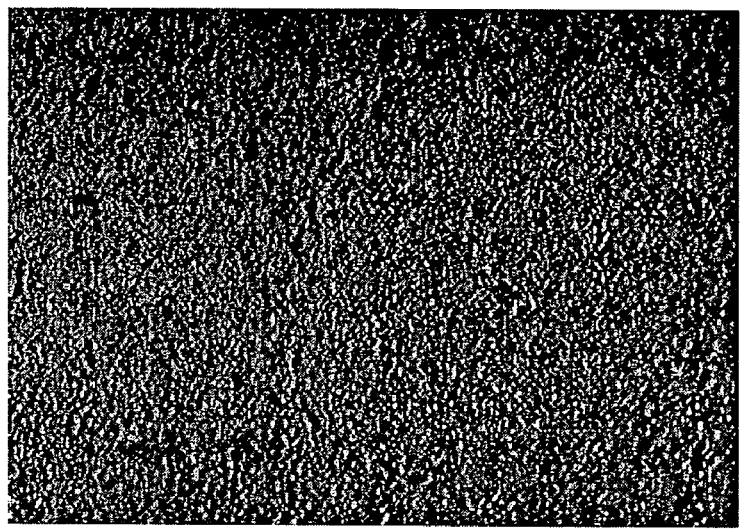
Figure 16:
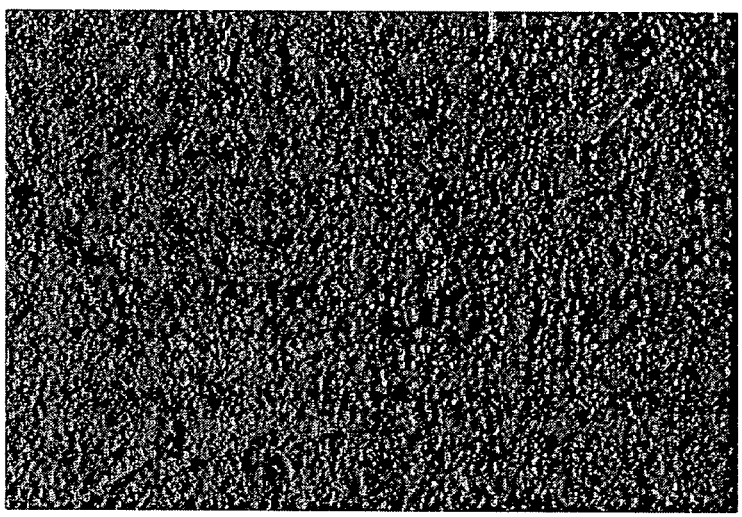
Figure 16:
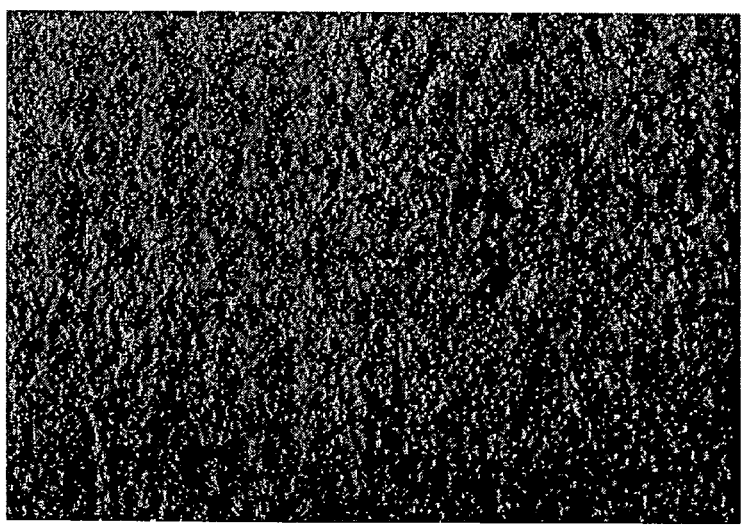

FIG. 16. Distribution of LPD/E7 particles in the spleen following IV administration. Spleens from mice that were injected with LPD/E7 particles containing Cy3 labeled ODN were visualized at the indicated times after administration.

Figure 17A:
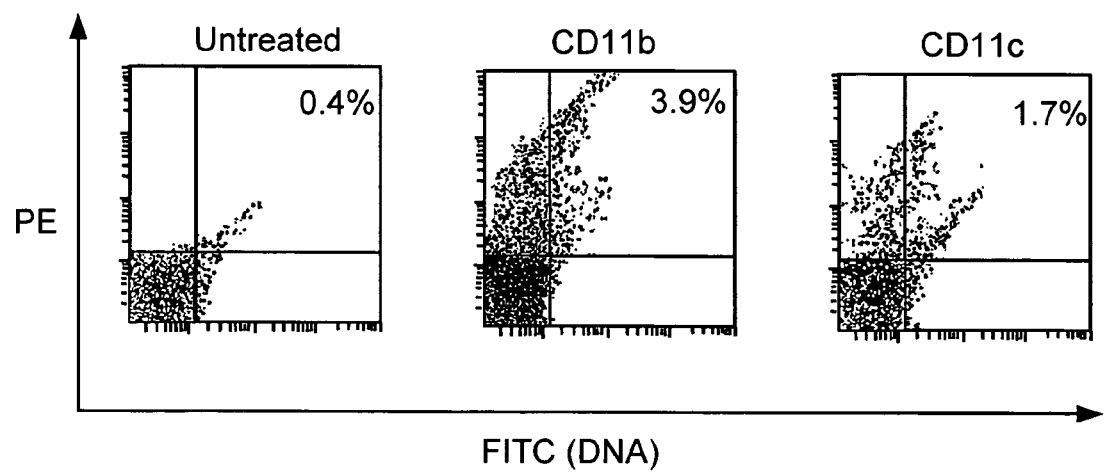
Figure 17B:
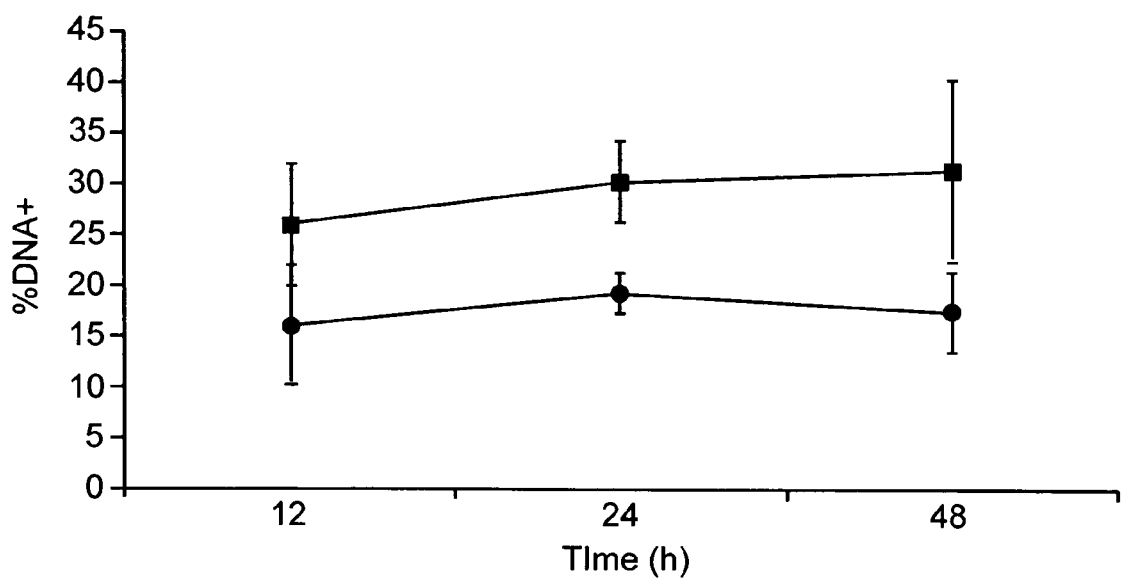

FIGS. 17A and 17B. Uptake of LPD/E7 particles by CD11b+ and CD11c+ cells. Mice were injected with LPD particles containing 25 µg pNGVL3, 0.1 µg FITC labeled ODN and 10 µg E7 peptide in 150 µl 5% dextrose. (A) Splenocytes were collected 24 h later, stained with PE labeled anti-CD11b or CD11c antibodies and analyzed by flow cytometry. (B) Spleens were collected at the indicated times post injection and the percent of all CD11b+ (■) and CD11c+ (●) that were DNA positive was determined. Mean±SD, n=3. One representative of 3 experiments is shown.

Figure 18A:
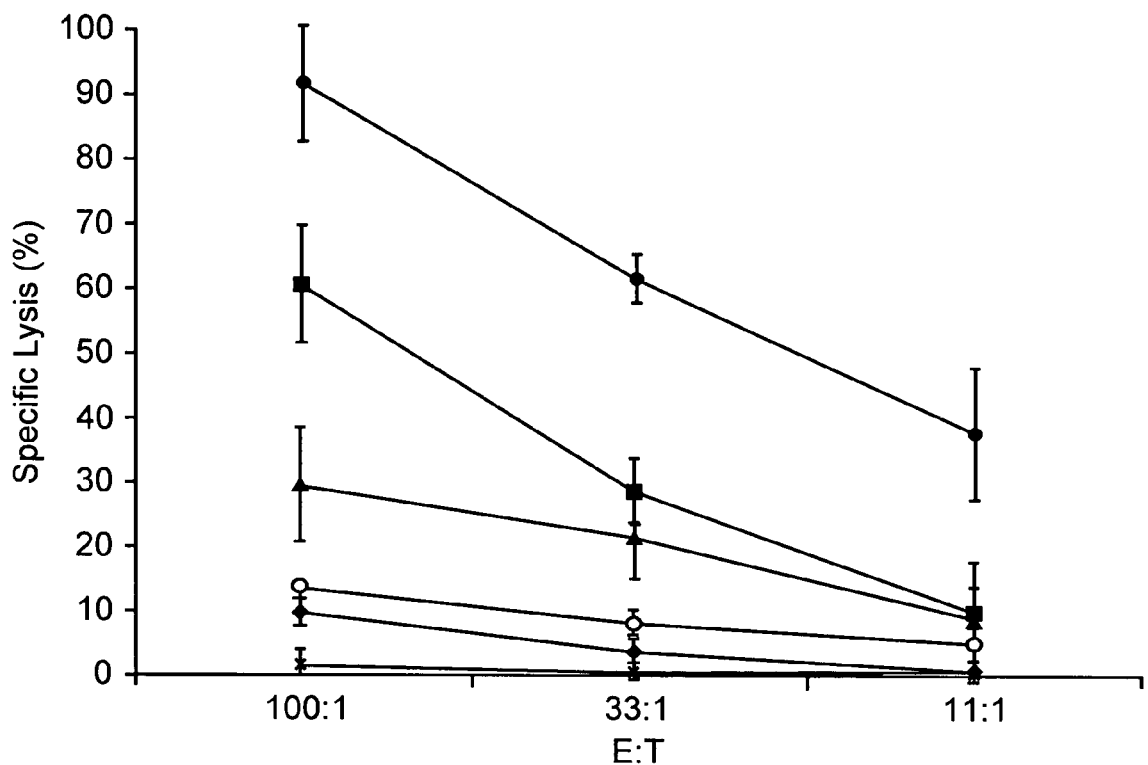
Figure 18B:
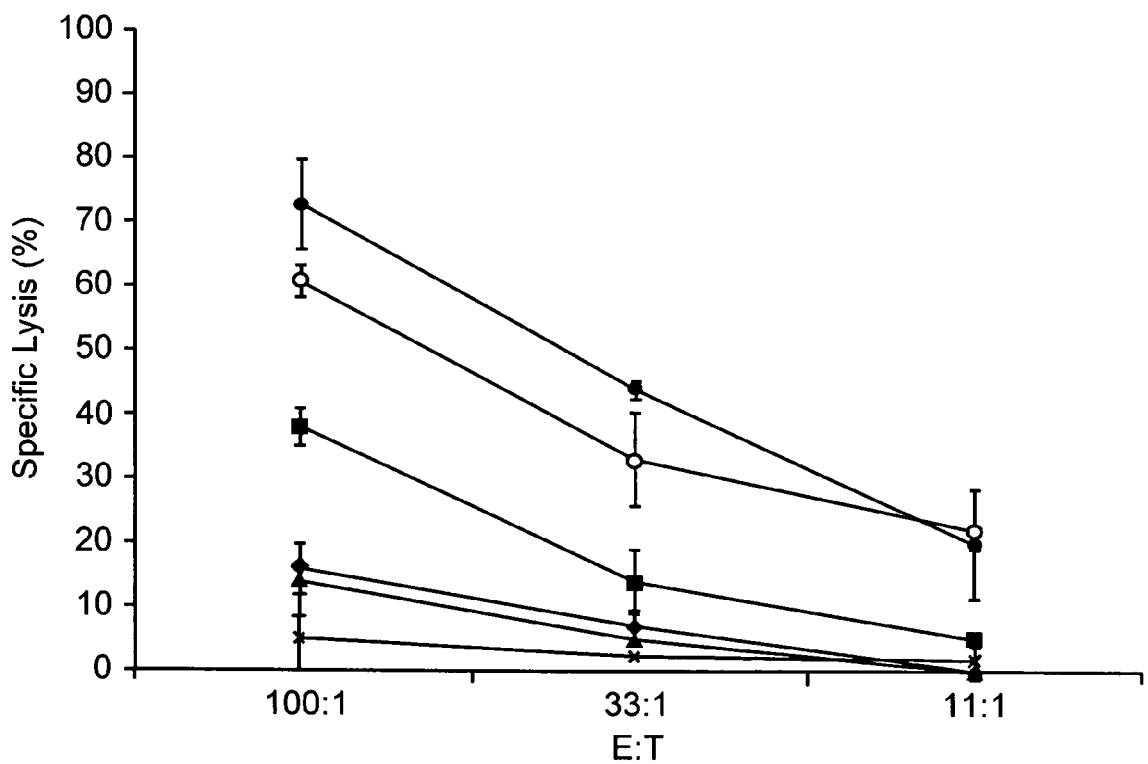

FIGS. 18A and 18B. Tumor specific CTL activity induced by LPD/E7 vaccination. Mice were IV (A) or SC (B) injected with either LPD particles containing 0 (◆), 1 (▼), 10 (■), or 20 (●) µg of E7 peptide, SL liposomes containing 20 µg E7 peptide (○), or 20 µg E7 peptide in PBS (✱) on days 0 and 5. Five days after the last injection, splenocytes were isolated, restimulated for 4 days and used as effectors in a chromium release assay. Non-specific lysis was <8% in all groups. Mean±SD, 2 mice/group. One representative of 2 experiments is shown.

Figure 19A:
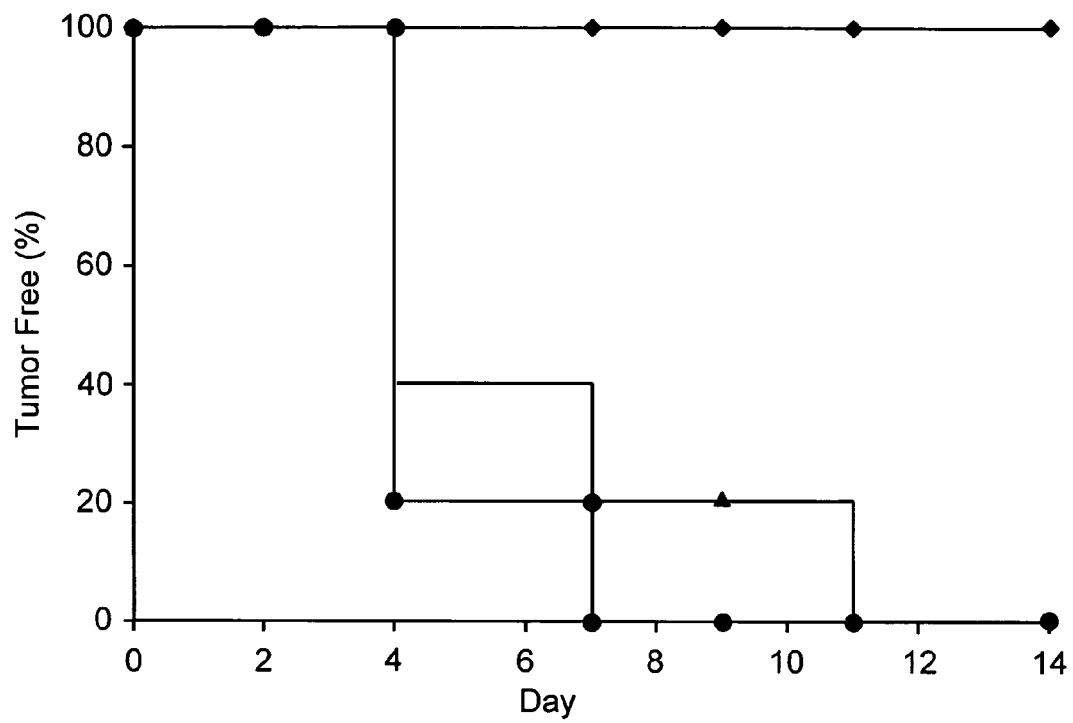
Figure 19B:
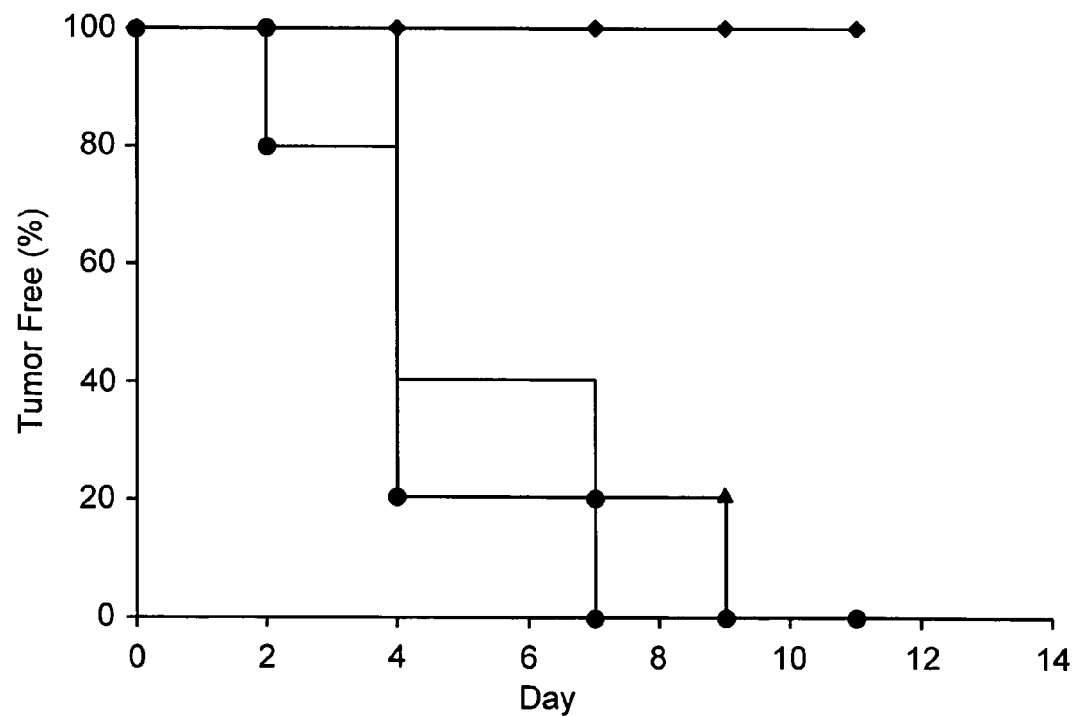

FIGS. 19A and 19B. LPD/E7 vaccination prevents tumor establishment. Mice were IV (A) or SC (B) injected with LPD particles with (●) or without (■) 20 µg E7 peptide, or 20 µg E7 peptide in PBS (◆) on days 0 and 5 or left untreated (▼). On day 10, the mice were SC challenged with 0.5×10⁶ TC-1 cells. Tumor formation was monitored twice per week by palpation. 5 mice per group. One representative of 3 experiments showing similar tumor formation kinetics is shown.

Figure 20A:
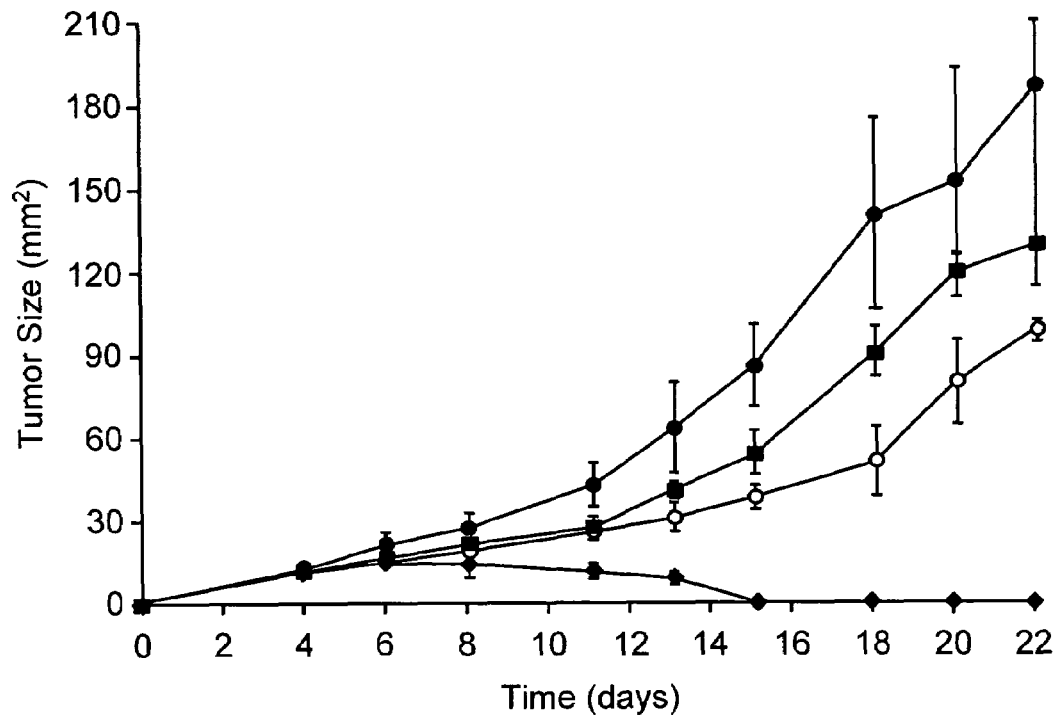
Figure 20B:
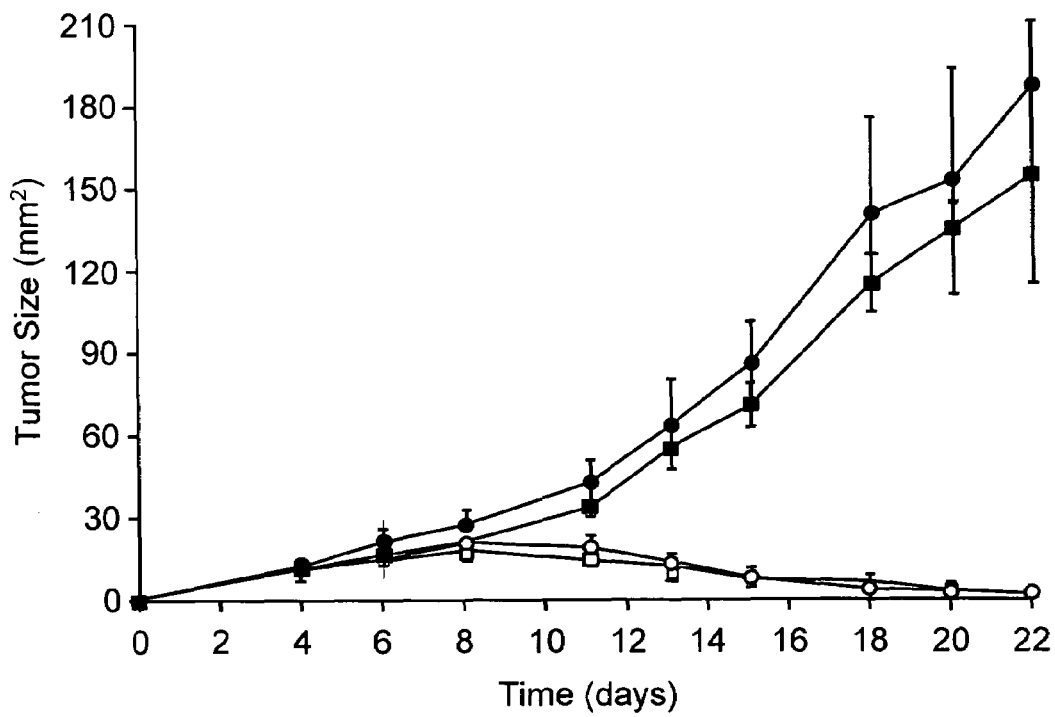

FIGS. 20A and 20B. LPD/E7 treatment eradicates established tumors. Intact (closed symbols) or asplenic mice (open symbols) were SC inoculated with 0.5×10⁶ TC-1 cells on day 0. On days 3 and 6, mice were or IV (A) or SC (B) injected with LPD particles with (●) or without (■) 10 µg E7 peptide or left untreated (◆). Tumor growth was measured 3 times per week. Mean±SD, 5 mice per group. One representative of 3 experiments showing similar tumor growth kinetics is shown.

Figure 21A:
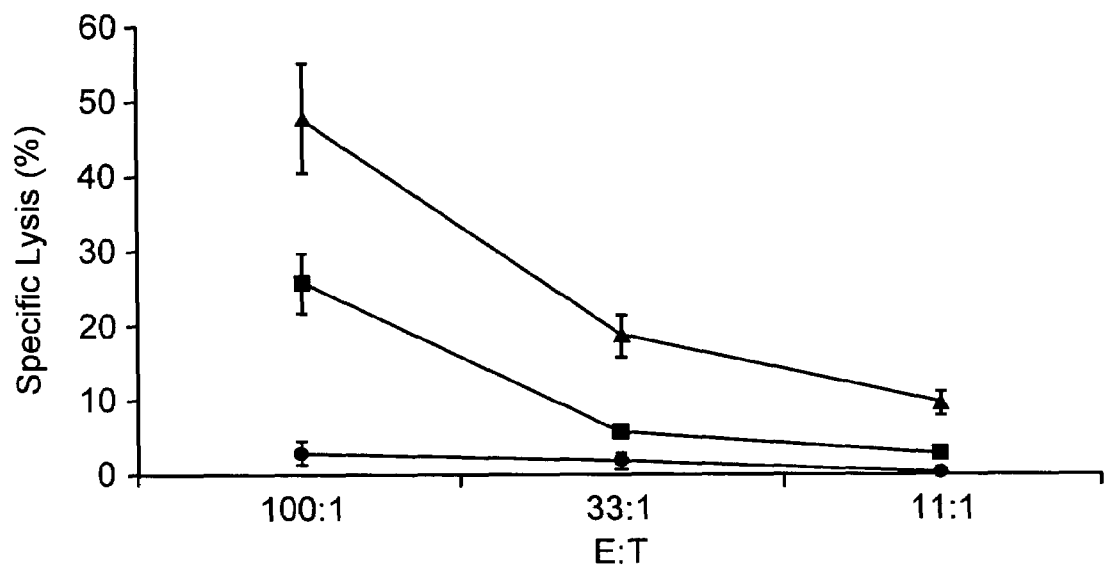
Figure 21B:
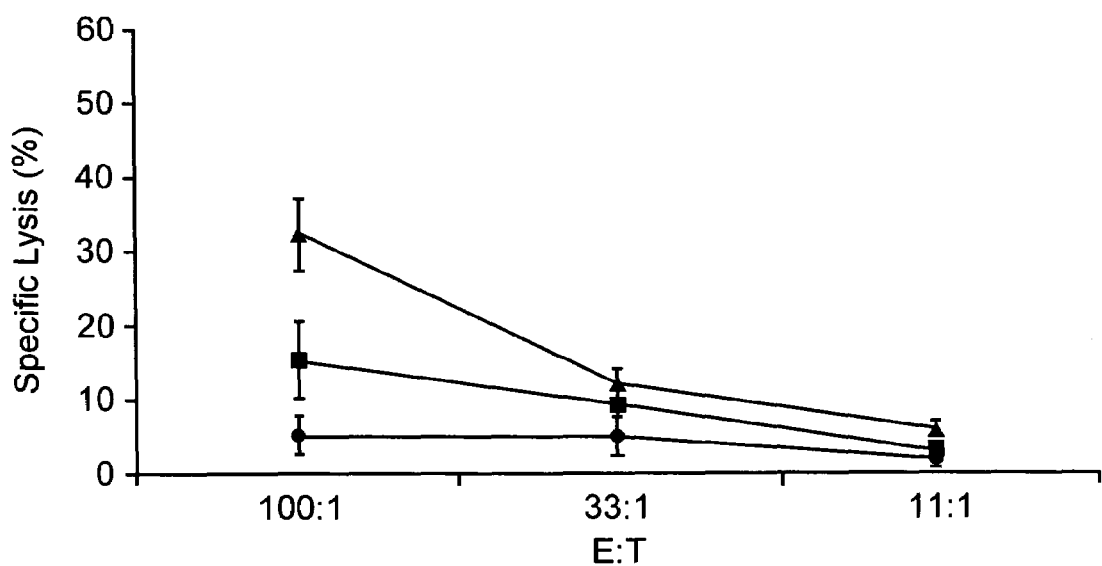

FIGS. 21A and 21B. Tumor specific CTL activity induced by LPD/E7 treatment. Tumor bearing mice were IV (A) or SC (B) treated with LPD particles with (▼) or without (■) 10 µg E7 peptide or E7 peptide in PBS (●). Ten days after the last treatment, splenocytes were isolated, restimulated for 4 days and used as effectors in a chromium release assay. EL4 cells pulsed with E7 peptide were used as specific targets. Non-specific lysis was <7% in all groups. Mean±SD, 2 mice per group. One representative of 2 experiments is shown.

DETAILED DESCRIPTION OF THE INVENTION

A. LPD Complexes

As mentioned, the present invention provides antigen/lipid/polycationic polypeptide salt complexes comprising an antigen, at least one lipid species and at least one polycationic polypeptide salt. LPD complexes are described in U.S. Pat. No. 6,008,202, which issued to Huang et al. on Dec. 28, 1999, the teachings of which are incorporated by reference. The teachings in U.S. Pat. No. 6,008,202 directed to LPD complexes are fully applicable to the present invention, except that it has now been surprisingly found that when an antigen is incorporated into the LPD, the antigen-LPD complex can be used as an effective vaccine to prevent and to treat cancers and other infectious diseases.

This invention relates to lipid-comprising antigen delivery complexes having a net positive charge and/or a positively charged surface at pH 6.0-8.0. These complexes comprise lipids, antigens and optionally further comprise polycations. The invention further relates to a method for producing these complexes where the method may optionally include the step of purifying these formulations from excess individual components. For the production of the antigen/LPD complexes of this invention, inclusion of the purification step is a preferred embodiment. The lipid-comprising antigen delivery complexes of this invention are stable, capable of being produced at relatively high concentrations, and retain biological activity of the antigen component over time in storage.

The "antigen" which is contained in the lipid-comprising drug delivery complexes of the present invention may be nucleic acids, polyanionic proteins, polysaccharides and other macromolecules which can be complexed directly with cationic lipids. However, cationic drugs (e.g., large cationic protein) can be directly complexed with an anionic lipid or sequentially complexed first with anionic lipid or polymer followed by cationic lipid. The use of this process permits delivery of positive or neutral charged drug to cells by the complexes of the present invention.

The cationic liposomes mixed with antigen or with antigen and polycation to form the complexes of the present invention may contain a cationic lipid alone or a cationic lipid in combination with a neutral lipid. Suitable cationic lipid species include, but are not limited to: 3-β[⁴N-(¹N,⁸N-diguanidino spermidine)-carbamoyl] cholesterol (BGSC); 3-β[N,N-diguanidinoethyl-aminoethane)-carbamoyl] cholesterol (BGTC); N,N¹,N²,N³ Tetra-methyltetrapalmityl-spermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2(sperminecarboxamido)ethyl]-N,N-dimethyl-1-propanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3 dioleoyloxy-1,4-butanediammonium iodide) (Tfx-50); 1,2 bis(oleoyloxy)-3-(trimethylammonio) propane (DOTAP); N-1-(2,3-dioleoyloxy) propyl-N,N,N-trimethyl ammonium chloride (DOTMA) or other N-(N,N-1-dialkoxy)-alkyl-N,N,N-trisubstituted ammonium surfactants; 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-β-hydroxyethylammonium) or DORIE (DL-1,2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, cholesteryl-3β-carboxyl-amido-ethylenetrimethylammonium iodide, 1-dimethylamino-3-trimethylammonio-DL-2-propyl-cholesteryl carboxylate iodide, cholesteryl-3-β-carboxyamido-ethyleneamine, cholesteryl-3-β-oxysuccinamido-ethylenetrimethylammonium iodide, 1-dimethylamino-3-trimethylammonio-DL-2-propyl-cholesteryl-3-β-oxysuccinate iodide, 2-(2-trimethylammonio)-ethylmethylamino ethyl-cholesteryl-3-β-oxysuccinate iodide, 3-β-N-(N',N'-dimethylaminoethane) carbamoyl cholesterol (DC-chol), and 3-β-N-(polyethyleneimine)-carbamoylcholesterol.

Examples of preferred cationic lipids include N-t-butyl-N'-tetradecyl-3-tetradecyl-aminopropion-amidine (CLONfectin), 2,3-dioleoyloxy-N-[2(sperminecarboxamido)ethyl]-N,N-dimethyl-1-propanaminium trifluoroacetate (DOSPA), 1,2-bis(oleoyloxy)-3-(trimethylammonio)propane (DOTAP), N-[1-(2,3, dioleoyloxy)propyl]-N,N,N-trimethylammonium chloride) (DOTMA), cholesteryl-3-β-carboxyamidoethylenetrimethylammonium iodide, 1-dimethylamino-3-trimethylammonio-DL-2-propyl-cholesteryl carboxylate iodide, cholesteryl-3-β-carboxyamidoethyleneamine, cholesteryl-3-β-oxysuccinamidoethylenetrimethylammonium iodide, 1-dimethylamino-3-trimethylammonio-DL-2-propyl-cholesteryl-3-β-oxysuccinate iodide, 2-(2-trimethylammonio)ethylmethylamino ethyl-cholesteryl-3-β-oxysuccinate iodide, 3-β-N-(N',N'dimethyl-aminoethane)-carbamoyl-cholesterol (DC-chol), and 3-β-N-(polyethyleneimine)-carbamoyl cholesterol.

In certain embodiments, it has been found that certain cationic lipids have an increased immunostimulatory effect, i.e., increased immunostimulation activity. It has surprisingly been found that cationic lipids having shorter acyl chains have increased immunostimulation activity. In addition, it has surprisingly been found that cationic lipids having cis-unsaturated double bonds have increased immunostimulation activity. As such, in preferred embodiments, the cationic lipids used in the antigen-LPD complexes of the present invention are those that have shorter acyl chains and, in addition, those that have cis-unsaturated double bonds.

Since an attribute of the complexes of the invention is their stability during storage (i.e., their ability to maintain a small diameter and retain biological activity over time following their formation), it will be understood by those of ordinary skill in the art that preferred cationic lipids are those lipids in which bonds between the lipophilic group and the amino group are stable in aqueous solution. While such bonds found in cationic lipids include amide bonds, ester bonds, ether bonds and carbamoyl bonds, preferred cationic lipids are those having a carbamoyl bond. An example of a preferred cationic lipid having a carbamoyl bond is DC-Chol. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed (Brunette, E. et al. (1992) Nucl. Acids Res., 20:1151).

It is to be further understood that in considering cationic liposomes suitable for use in mixing with antigen and optionally with polycation, to form the complexes of this invention, the methods of the invention are not restricted only to the use of the cationic lipids recited above but rather, any lipid composition may be used so long as a cationic liposome is produced.

Thus, in addition to cationic lipids, cationic liposomes used to form the complexes of the invention may contain other lipids in addition to the cationic lipids. These lipids include, but are not limited to, lyso lipids of which lyso-phosphatidylcholine (1-oleoyl lysophosphatidylcholine) is an example, cholesterol, or neutral phospholipids including dioleoyl phosphatidyl ethanolamine (DOPE) or dioleoyl phosphatidylcholine (DOPC) as well as various lipophylic surfactants, containing polyethylene glycol moieties, of which Tween-80 is one example. The lipid complexes of the invention may also contain negatively charged lipids as well as cationic lipids so long as the net charge of the complexes formed is positive and/or the surface of the complex is positively charged. Negatively charged lipids of the invention are those comprising at least one lipid species having a net negative charge at or near physiological pH or combinations of these. Suitable negatively charged lipid species include, but are not limited to, CHEMS (cholesteryl hemisuccinate), NGPE (N-glutaryl phosphatidlylethanolanine), phosphatidyl glycerol and phosphatidic acid or a similar phospholipid analog.

It is further contemplated that in the cationic liposomes utilized to form the complexes of the invention, the ratio of lipids may be varied to include a majority of cationic lipids in combination with cholesterol or with mixtures of lyso or neutral lipids. When the cationic lipid of choice is to be combined with another lipid, a preferred lipid is a neutral phospholipid, most preferably DOPE.

Methods for producing the liposomes to be used in the production of the lipid comprising drug delivery complexes of the present invention are known to those of ordinary skill in the art. A review of methodologies of liposome preparation may be found in Liposome Technology (CFC Press New York 1984); Liposomes by Ostro (Marcel Dekker, 1987); Methods Biochem Anal. 33:337-462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the drug/lipid complexes of this invention, the cationic lipid is present in the liposome at from about 10 to about 100 mole % of total liposomal lipid, preferably from about 20 to about 80 mole % and most preferably about 20 to about 60 mole %. The neutral lipid, when included in the liposome, may be present at a concentration of from about 0 to about 90 mole % of the total liposomal lipid, preferably from about 20 to about 80 mole %, and most preferably from 40 to 80 mole %. The negatively charged lipid, when included in the liposome, may be present at a concentration ranging from about 0 mole % to about 49 mole % of the total liposomal lipid, preferably from about 0 mole % to about 40 mole %. In a preferred embodiment, the liposomes contain a cationic and a neutral lipid, most preferably DC-Chol and DOPE in ratios between about 2:8 to about 6:4. It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Potential targets include, but are not limited to, liver, blood cells, endothelial cells and tumor cells. Furthermore, to enhance the circulatory half-life of the complexes, the positive surface charge can be sterically shielded by incorporating lipophilic surfactants which contain polyethylene glycol moieties.

It is to be further understood that the positive charge of the complexes of this invention may be affected not only by the lipid composition of the complex, but also by the pH of the solution in which the drug/lipid complexes are formed. For example, increasing pH (more basic) will gradually neutralize the positive charge of the tertiary amine of the cationic lipid DC-Chol. In a preferred embodiment, the complexes of the present invention are produced, and stored, at a pH such that the complexes have a net positive charge and/or positively charged surface. A preferred pH range is pH 6.0-8.0, most preferably pH 7.0-7.8.

When a polycation is to be mixed with nucleic acid and cationic liposomes, the polycation may be selected from organic polycations having a molecular weight of between about 300 and about 200,000. These polycations also preferably have a valence of between about 3 and about 1000 at pH 7.0. The polycations may be natural or synthetic amino acids, peptides, proteins, polyamines, carbohydrates and any synthetic cationic polymers. Non-limiting examples of polycations include polyarginine, polyornithine, protamines and polylysine, polybrene (hexadimethrine bromide), histone, cationic dendrimer, spermine, spermidine and synthetic polypeptides derived from SV40 large T antigen which has excess positive charges and represents a nuclear localization signal. In one embodiment, the polycation is poly-L-lysine (PLL).

In another more preferred embodiment, the polycation is a polycationic polypeptide having an amino acid composition in which arginine residues comprise at least 30% of the amino acid residues of the polypeptide and lysine residues comprise less than 5% of the amino acid residues of the polypeptide. In addition, preferably histidine, lysine and arginine together make up from about 45% to about 85% of the amino acid residues of the polypeptide and serine, threonine and glycine make up from about 10% to about 25% of the amino acid residues of the polypeptide. More preferably, arginine residues constitute from about 65% to about 75% of the amino acid residues of the polypeptide and lysine residues constitute from about 0 to about 3% of the amino acid residues of the polypeptide.

In addition to the above recited percentages of arginine and lysine residues, the polycationic polypeptides of the invention may also contain from about 20% to about 30% hydrophobic residues, more preferably, about 25% hydrophobic residues. The polycationic polypeptide to be used in producing drug/lipid/polycation complexes may be up to 500 amino acids in length, preferably about 20 to about 100 amino acids in length; more preferably, from about 25 to about 50 amino acids in length, and most preferably from about 25 to about 35 amino acids in length.

In one embodiment, the arginine residues present in the polycationic polypeptide are found in clusters of 3-8 contiguous arginine residues and more preferably in clusters of 4-6 contiguous arginine residues.

In another embodiment, the polycationic polypeptide is about 25 to about 35 amino acids in length and about 65 to about 70% of its residues are arginine residues and 0 to 3% of its residues are lysine residues.

The polycationic polypeptides to be used in formulating the complexes of the invention may be provided as naturally occurring proteins, particularly certain protamines having a high arginine to lysine ratio as discussed above, as a chemically synthesized polypeptide, as a recombinant polypeptide expressed from a nucleic acid sequence which encodes the polypeptide, or as a salt of any of the above polypeptides where such salts include, but are not limited to, phosphate, chloride and sulfate salts.

The complexes formed by the methods of the present invention are stable for up to about one year when stored at 4° C. The complexes may be stored in 10% sucrose or a 5% dextrose solution upon collection from the sucrose gradient or they may be lyophilized and then reconstituted in an isotonic solution prior to use. In a preferred embodiment, the complexes are stored in solution. The stability of the complexes of the present invention is measured by specific assays to determine the physical stability and biological activity of the complexes over time in storage. The physical stability of the complexes is measured by determining the diameter and charge of the complexes by methods known to those of ordinary skill in the art, including for example, electron microscopy, gel filtration chromatography or by means of quasi-elastic light scattering using, for example, a Coulter N4SD particle size analyzer as described in the Examples. The physical stability of the complex is "substantially unchanged" over storage when the diameter of the stored complexes is not increased by more than 100%, preferably by not more than 50%, and most preferably by not more than 30%, over the diameter of the complexes as determined at the time the complexes were purified.

Therapeutic formulations using the complexes of the invention preferably comprise the complexes in a physiologically compatible buffer such as, for example, phosphate buffered saline, isotonic saline or low ionic strength buffer such as 10% sucrose in $H_2O$ (pH 7.4-7.6) or in Hepes (pH 7-8, a more preferred pH being 7.4-7.6). The complexes may be administered as aerosols or as liquid solutions for intratumoral, intravenous, intratracheal, intraperitoneal, and intramuscular administration.

Methods for preparing and purifying the antigen-LPD complexes of the present invention are disclosed in U.S. Pat. No. 6,008,202, the teachings of which are incorporated by reference.

B. Antigens

A "tumor-associated antigen," as used herein is a molecule or compound (e.g., a protein, peptide, polypeptide, lipid, glycolipid, carbohydrate and/or DNA) associated with a tumor or cancer cell and which is capable of provoking an immune response when expressed on the surface of an antigen presenting cell in the context of an MHC molecule. Tumor-associated antigens include self antigens, as well as other antigens that may not be specifically associated with a cancer, but nonetheless enhance an immune response to and/or reduce the growth of a tumor or cancer cell when administered to an animal. More specific embodiments are provided herein.

A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In a preferred embodiment, a compound is similar to a naturally-occurring microorganism antigen if it induces an immune response (humoral and/or cellular) similar to a naturally-occurring microorganism antigen. Compounds or antigens that are similar to a naturally-occurring microorganism antigen are well known to those of ordinary skill in the art. A non-limiting example of a compound that is similar to a naturally-occurring microorganism antigen is a peptide mimic of a polysaccharide antigen. More specific embodiments are provided herein.

The term "antigen" is further intended to encompass peptide or protein analogs of known or wild-type antigens such as those described above. The analogs may be more soluble or more stable than wild type antigen, and may also contain mutations or modifications rendering the antigen more immunologically active. Also useful in the compositions and methods of the present invention are peptides or proteins which have amino acid sequences homologous with a desired antigen's amino acid sequence, where the homologous antigen induces an immune response to the respective tumor.

In one embodiment, the antigen in the LPD complex comprises an antigen associated with a tumor or cancer, i.e., a tumor-associated antigen. As such, in a preferred embodiment, the tumor or cancer vaccines of the present invention further comprise at least one epitope of at least one tumor-associated antigen. In another preferred embodiment, the tumor or cancer vaccines of the present invention further comprise a plurality of epitopes from one or more tumor-associated antigens. The tumor-associated antigens finding use in the LPD complexes and methods of the present invention can be inherently immunogenic, or non-immunogenic, or slightly immunogenic. As demonstrated herein, even tumor-associated self antigens may be advantageously employed in the subject vaccines for therapeutic effect, since the subject compositions are capable of breaking immune tolerance against such antigens. Exemplary antigens include, but are not limited to, synthetic, recombinant, foreign, or homologous antigens, and antigenic materials may include but are not limited to proteins, peptides, polypeptides, lipids, glycolipids, carbohydrates and DNA.

Tumor-associated antigens suitable for use in the subject invention include both mutated and non-mutated molecules which may be indicative of single tumor type, shared among several types of tumors, and/or exclusively expressed or overexpressed in tumor cells in comparison with normal cells. In addition to proteins and glycoproteins, tumor-specific patterns of expression of carbohydrates, gangliosides, glycolipids and mucins have also been documented. Moingeon, supra. Exemplary tumor-associated antigens for use in the subject cancer vaccines include protein products of oncogenes, tumor suppressor genes and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins and a number of other self proteins.

Specific embodiments of tumor-associated antigens include, e.g., mutated antigens such as the protein products of the Ras p21 protooncogenes, tumor suppressor p53 and HER-2/neu and BCR-ab1 oncogenes, as well as CDK4, MUM1, Caspase 8, and Beta catenin; overexpressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy.

In fact, in a preferred embodiment, the human papillomavirus (HPV) subtype 16 E7 is used as the tumor-associated antigen. It has been found that E7 antigen-LPD complexes of the present invention are effective at preventing and treating cervical cancer. In addition, the present invention provides a genetically engineered E7 protein, i.e., E7m protein, having antigenic activity, but without tumorigenic activity. It has been found that the E7m-LPD complexes of the present invention induce cellular immunity to cause complete regression of established tumors and, thus, can be used as potent anti-cervical cancer vaccines.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously included in the cancer vaccines of the present invention. It is estimated that close to 16% of the worldwide incidence of cancer can be attributed to infectious pathogens; Moingeon, supra, and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use in the cancer vaccines provided herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, Great Britain 1983, the entire contents of which is hereby incorporated by reference.

In another embodiment, the antigen in the LPD complex comprises an antigen derived from or associated with a pathogen, i.e., a microbial antigen. As such, in a preferred embodiment, the pathogen vaccines of the present invention further comprise at least one epitope of at least one microbial antigen. Pathogens which may be targeted by the subject vaccines include, but are not limited to, infectious virus, infectious bacteria, infectious parasites and infectious fungi. In another preferred embodiment, the pathogen vaccines of the present invention further comprise a plurality of epitopes from one or more microbial antigens.

The microbial antigens finding use in the subject compositions and methods may be inherently immunogenic, or non-immunogenic, or slightly immunogenic. Exemplary antigens include, but are not limited to, synthetic, recombinant, foreign, or homologous antigens, and antigenic materials may include but are not limited to proteins, peptides, polypeptides, lipids, glycolipids, carbohydrates and DNA.

Exemplary viral pathogens include, but are not limited to, infectious virus that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and gram positive bacteria may be targeted by the subject compositions and methods in vertebrate animals. Such gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris*, *Borella burgdorferi*, *Legionella pneumophilia*, *Mycobacteria* sps (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*, pathogenic *Campylobacter* sp., *Enterococcus* sp., *Haemophilus infuenzae*, *Bacillus antracis*, *corynebacterium diphtheriae*, *corynebacterium* sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* sp., *Fusobacterium nucleatum*, *Streptobacillus moniliformis*, *Treponema pallidium*, *Treponema pertenue*, *Leptospira*, *Rickettsia*, and *Actinomyces israelli*.

Polypeptides of bacterial pathogens which may find use as sources of microbial antigens in the subject compositions include but are not limited to an iron-regulated outer membrane protein, ("IROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of Yersiniosis; an extracellular protein ("ECP"), an iron-regulated outer membrane protein ("IROMP"), and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of *Rickettsia*. Such antigens can be isolated or prepared recombinantly or by any other means known in the art.

Examples of pathogens further include, but are not limited to, infectious fungi that infect mammals, and more particularly humans. Examples of infectious fungi include, but are not limited to: *Cryptococcus neoformans*, *Histoplasma capsulatum*, *Coccidioides immitis*, *Blastomyces dermatitidis*, *Chlamydia trachomatis*, *Candida albicans*. Examples of infectious parasites include *Plasmodium* such as *Plasmodium falciparum*, *Plasmodium malariae*, *Plasmodium ovale*, and *Plasmodium vivax*. Other infectious organisms (i.e. protists) include *Toxoplasma gondii*. Polypeptides of a parasitic pathogen include but are not limited to the surface antigens of Ichthyophthirius.

Other medically relevant microorganisms that serve as antigens in mammals and more particularly humans are described extensively in the literature, e.g., see C. G. A Thomas, Medical Microbiology, Bailliere Tindall, Great Britain 1983, the entire contents of which is hereby incorporated by reference. In addition to the treatment of infectious human diseases and human pathogens, the compositions and methods of the present invention are useful for treating infections of nonhuman mammals. Many vaccines for the treatment of non-human mammals are disclosed in Bennett, K. Compendium of Veterinary Products, 3rd ed. North American Compendiums, Inc., 1995; see also WO 02/069369, the disclosure of which is expressly incorporated by reference herein.

Exemplary non-human pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

In preferred embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse.

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

EXAMPLE I

LPD as a Vaccine Delivery System

1. Subcutaneously Injected LPD/peptide Complex Accumulates in Local Lymphnode and Taken up by Various Immune Effector Cells.

As delivery to organized lymph tissue is important for successful vaccination, we wished to determine if LPD particles would make their way into draining lymph nodes following subcutaneous injection. C57BL/6 mice were footpad injected with LPD/E7 particles containing trace amounts of Cy5-labled DNA. At 16 h after injection, popliteal lymph nodes were collected, single cell suspensions were prepared and LPD the percentage of cells that took up LPD was determined by flow cytometry. Mice injected with non-fluorescent LPD particles served as controls. After SC administration, 2.4% of all lymph node cells took up LPD particles. While only a small percentage of all lymph node cells take up LPD particles, this can be sufficient to produces effective vaccination of those cells are capable of effectively presenting the delivered antigen. To determine what cell types were taking up LPD/E7 particles, C57BL/6 mice were footpad injected with LPD/E7 particles containing trace amounts of Cy5-labeled DNA. At 16 h after injection, popliteal LN cells were stained for the cell-type specific surface markers CD11b (to identify macrophages and myeloid lineage DCs), CD11c (to identify dendritic cells), CD19 (to identify B cells), and NK1.1 (to identify NK cells) using fluorescently labeled antibodies and subjected to flow cytometric analysis. Phagocytic cells appear to be the main cell types that take up LPD/antigen particles with high percentage of NK cells (25%) and macrophages (25%) taking up particles while only 2.4% of B cells took up LPD particles. Of particular interest, 16.8% of dendritic cells took up LPD particles (Please see data in the table in Dileo et al.).

2. LPD/E7 Complexes Induce an E7 Specific Immune Response.

To determine if LPD/E7 particles induce enhanced immunization versus traditional liposome/peptide vaccines, mice were SC or IV vaccinated with LPD particles containing 0, 1, 10, or 20 µg of E7 peptide on days 0 and 5. For comparison, mice were injected with 20 µg E7 peptide in PBS or encapsulated in SL liposomes. Five days after the final vaccination, splenocytes were collected, and used as effector cells in a chromium release assay. Consistent with previous reports, antigen containing SL liposomes induced significant levels of CTL activity (61% specific lysis) following SC injection only. Vaccination with 20 µg LPD/E7 produced the highest levels of CTL activity by both routes. Injection of 10 µg LPD/E7 particles induced intermediate levels of CTL activity in both cases, while 1 µg LPD/E7 induced significant CTL activity following IV administration only (Dileo et al.).

3. LPD/E7 Induces Both Protective and Therapeutic Immunities Against HPV+ Tumor.

To determine if the induced immune response is adequate to provide protective immunity, mice were IV or SC vaccinated with either 20 µg E7 peptide in PBS, empty LPD, or LPD containing 20 µg of E7 peptide on days 0 and 5. Untreated mice served as controls. Five days after the last vaccination, mice were SC challenged with $0.5 \times 10^6$ E7 expressing TC-1 cells. Mice that received LPD/E7 particles by either route failed to develop tumors, while control mice and mice that received LPD alone or free E7 peptide developed tumors within 12 days (Dileo et al.). To determine the potential of LPD/E7 complex for use as a therapeutic strategy, subcutaneous tumors were established in C57BL/6 mice by inoculation of $0.5 \times 10^6$ TC-1 cells.

On days 3 and 6 following inoculation, mice were injected IV or SC with LPD containing 10 µg of E7 peptide. To determine the importance of antigen delivery to the spleen in the generation of the observed immune responses, a group of mice that had their spleens surgically removed was included. Untreated mice and mice receiving empty LPD served as controls. All mice that received IV LPD/E7 peptide showed steady tumor shrinkage and complete regression within 2 weeks. SC treatment also resulted in complete regression but with slower kinetics. As expected, empty LPD administration slowed tumor progression but failed to eradicate the tumors. The anti-tumor effect in asplenic mice depended on the route of administration. IV treatment showed tumor growth rates similar to those observed in mice treated with LPD alone, while SC delivery resulted in tumor regression. Untreated mice showed unimpeded tumor progression (Dileo et al.). It has been shown that LPD administration to tumor bearing mice induces non-specific immune activation that can result in tumor regression. To confirm that tumor regression was due to an E7 specific response, ten days after the last treatment splenocytes were assayed for E7 specific tumor lytic activity. Consistent with previously published results, IV or SC injection of LPD without peptide induced a low level of apparent CTL activity while treatment with LPD/E7 resulted in the highest level of CTL activity in both cases (data not shown). Cells from untreated mice showed no lytic activity (Dileo et al., *Molecular Therapy*, 7(5):640-648 (May 2003), a copy of which was attached to the U.S.

Provisional Patent Application No. 60/567,291 as Appendix A, which is incorporated herein by reference for all purposes (herein after "Dileo, et al.").

4. A Single s.c. Injection of LPD/E7 can Induce Regression of Large Advanced Tumor.

Figure 1:
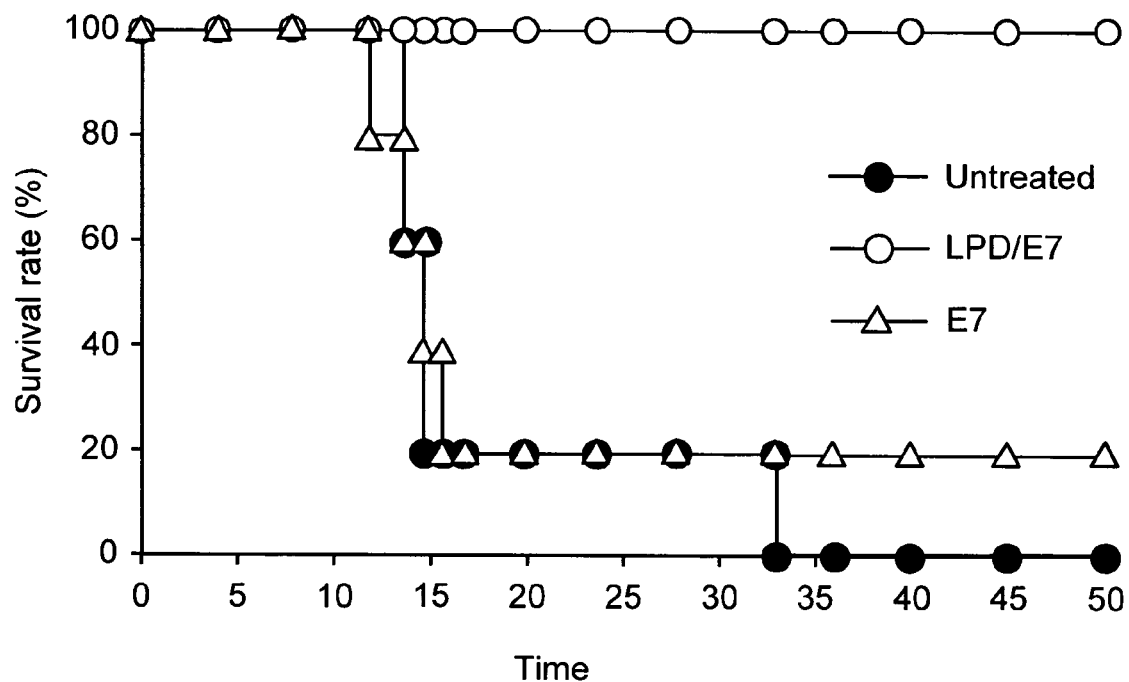
FIG. 1. One time treatment of LPD/E7 nanoparticles eradicates established tumors. C57BL/6 mice were s.c. inoculated with $1 \times 10^5$ TC-1 cells on day 4, 6, 8, or 12, mice were s.c. injected with LPD nanoparticles containing 10 μg of E7 peptide. Tumor growth was measured three times per week. Mean±SD, 5 mice per group. One representative of three experiments showing similar tumor growth kinetics is shown.

To determine how late the LPD/E7 nanoparticle treatment can still be effective, subcutaneous tumors were established in C57BL/6 mice by inoculation of $1\times10^5$ TC-1 cells. On days 4, 6, 8 or 12 following inoculation, mice were s.c. injected with LPD containing 10 μg of E7 peptide. Untreated mice served as control. Our data demonstrate that even a single injection of LPD/E7 nanoparticles as late as 8 days after tumor inoculation could still induce tumor regression in most of the treated animals (FIG. 1). LPD treatment on 12 days after TC-1 cell inoculation stopped tumor growth after 20 days. The experiment had to be terminated at 25 days because the size of the tumors in the untreated control group had grown to be too large. The average diameter of tumor on day 12 was more than 7 mm and this time point was at the middle of the entire course of the experiment. These data indicate that LPD/E7 nanoparticles may not only provide potent anti-tumor effects in vaccination protocols, but also be effective for the treatment of advanced tumors.

5. LPD/E7 is Effective in Treating Metastatic Tumor Model and Induce Tumor Specific Memory Immune Response.

Figure 2:
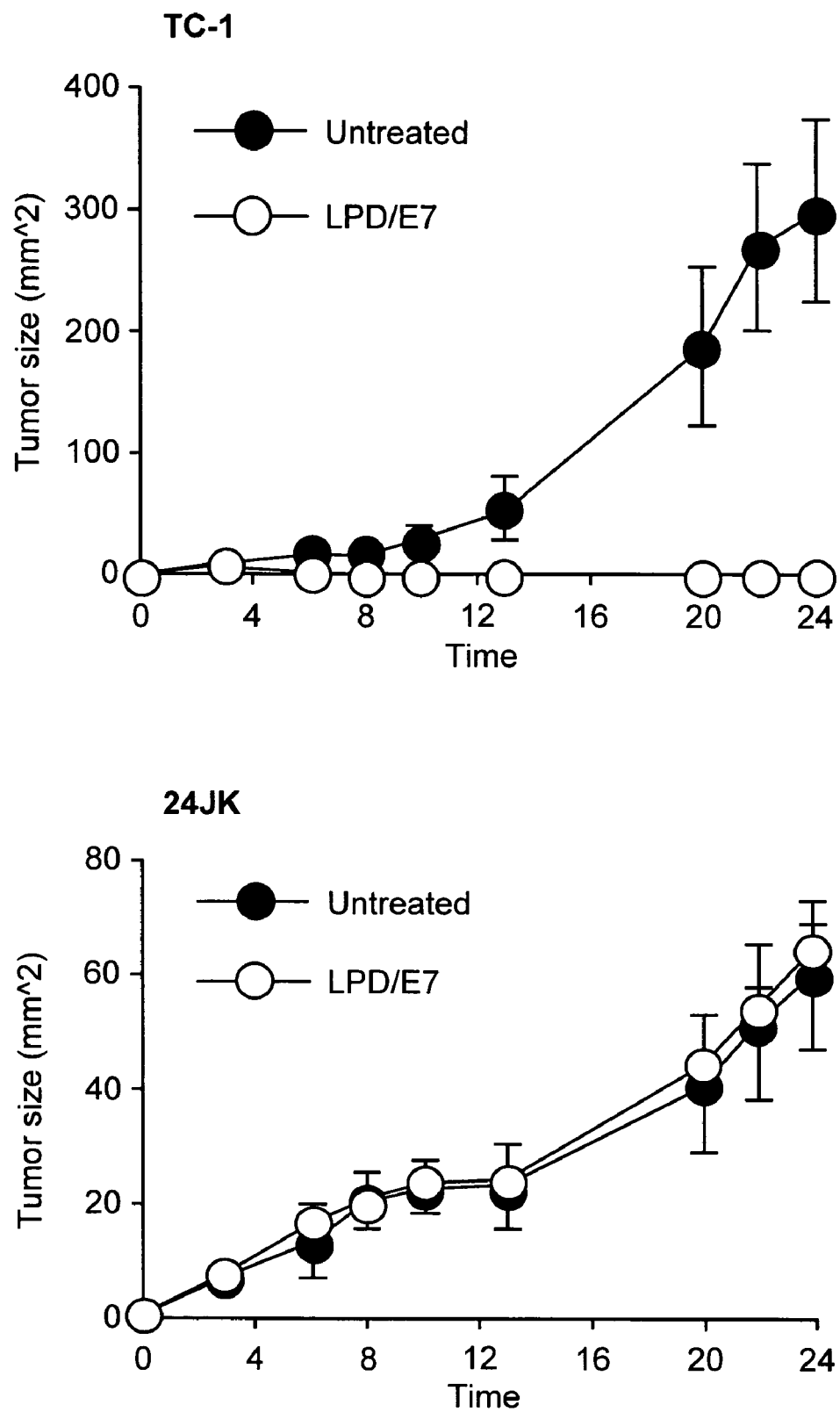
FIG. 2. LPD/E vaccination prevents tumor establishment after i.p. injection of TC-1 cells (A) and induces tumor specific immune response (B). A. Mice were s.c. injected with LPD particles with 10 μg E7 peptide or 10 μg E7 peptide in PBS on days 0 and 5 or left untreated. On day 10, the mice were i.p. challenged with $1 \times 10^6$ TC-1 cells and the survival rate was checked. B. 50 days after, the survived mice were s.c. rechallenged with $1 \times 10^5$ TC-1 or 24 JK cells. Tumor formation was monitored three times per week by palpation.

To identify the effect of LPD/E7 nanoparticle vaccination on the metastatic cervical cancer, we established metastatic tumor model with TC-1 cells. If TC-1 cells ($1\times10^6$ cells) were injected intraperitoneally, numerous metastatic tumor nodules were observed in the peritoneum in a few days later; many were also found in organs such as liver, spleen, kidney and lymph nodes. Inoculated mice died within 20 days after TC-1 cell injection (FIG. 2A). To determine if LPD/E7 vaccination induced anti-tumor immunity against i.p. injected TC-1 cells, mice were vaccinated with LPD particles containing 10 μg E7 peptide or 10 μg E7 peptide in PBS on day 0 and 5. On day 10, mice received subcutaneous tumor challenge at a dose of $1\times10^6$ TC-1 cells per mouse and the survival rate was measured. As shown in FIG. 2A, only 20% of untreated and E7-alone injected mice survived beyond 20 days after TC-1 cell injection, but the survival rate of LPD/E7 vaccinated group was 100% for the entire course of the experiment (50 days). To identify if survived mice from the LPD/E7 vaccination group exhibited the antigen specific immune response, mice were re-challenged subcutaneously with $1\times10^5$ TC-1 cells or 24 JK cells. Normal unvaccinated animals receiving an equal number of TC-1 cells or 24 JK cells were used as control groups. Mice that survived from first challenge with TC-1 cells also failed to develop tumors upon re-challenge with fresh TC-1 cells, while normal animals injected with TC-1 cells and all mice injected with 24 JK cells developed tumors (FIG. 2B). The data indicate that the immune response induced by LPD/E7 not only protected mice against the metastatic tumor challenge, but also provided protection for subsequent challenge.

6. Immunological Characterizations of LPD/E7 Peptide.

Figure 3:
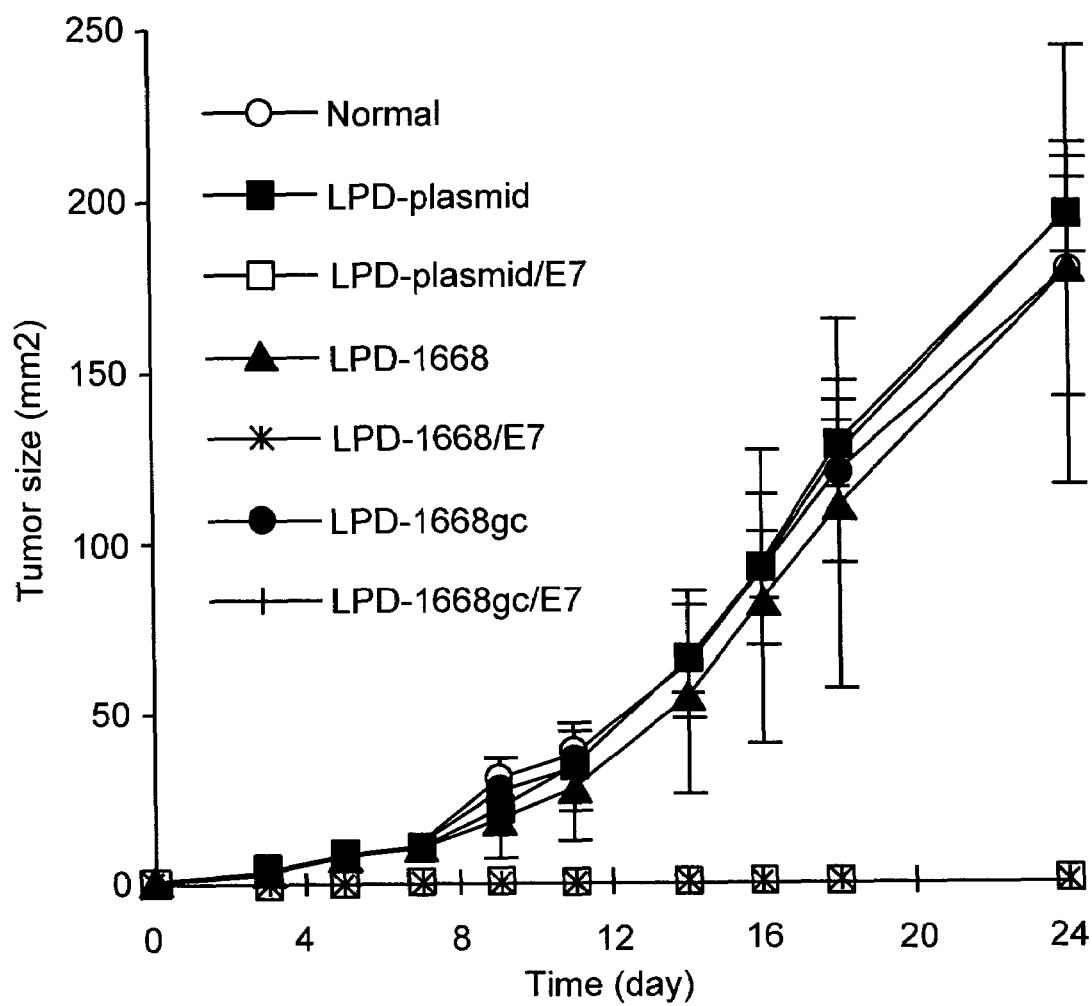
FIG. 3. All E7 peptide containg LPD nanoparticles can induce antigen specific anti tumor effect. Mice (n=5) were sc injected with LPD nanoparticles on day 0 and 5. On day 10, the mice were sc challenged with $1 \times 10^5$ TC-1 cells. Tumor formation was monitored three times per week.

Previous experiments showed that LPD particles formulated with ODN-1668 (containing unmethylated CpG motif), but not ODN-1668GC (containing identical sequence as 1668 except the CpG in the motif was replaced with GpC), could induce $TH_1$ cytokines and show anti-tumor activity (Whitmore et al, 2001). These experiments were done with LPD particles without any specific tumor antigen. Whether the same result would be true for an antigen specific vaccine activity was not known. We prepared LPD/E7 complex using either ODN-1668 or ODN-1668GC, but no plasmid DNA, and injected them to animals and to see if any protective immunity was developed in the animal against subsequent challenge of TC-1 cells. As can be seen in FIG. 3, all formulations containing E7 peptide had prevented the growth of tumor; whereas no formulations without E7 peptide had any activity. The data indicate that the antitumor activity was antigen dependent. Furthermore, since formulations with or without the CpG motif had the same activity, it suggested that the unmethylated CpG motif played little if any role in the induction of antitumor immune responses. This was a somewhat surprising result, because we had previously shown that CpG motifs are necessary for an antigen independent antitumor activity of LPD (Whitmore et al, 2001). Apparently, when the antigen is present, the antigen dependent immune response dominates the independent response. Moreover, the data also suggest that DNA or ODN is not necessary for the antitumor immune response. As long as the antigen, E7 peptide in this case, is carried by the cationic lipids, it can elicit an antitumor response. This hypothesis was independently verified by another experiment in which various LPD components were tested for antitumor activity. Indeed, E7 peptide complexed with DOTAP/chol liposomes could induce tumor regression after a single s.c. injection.

Figure 4:
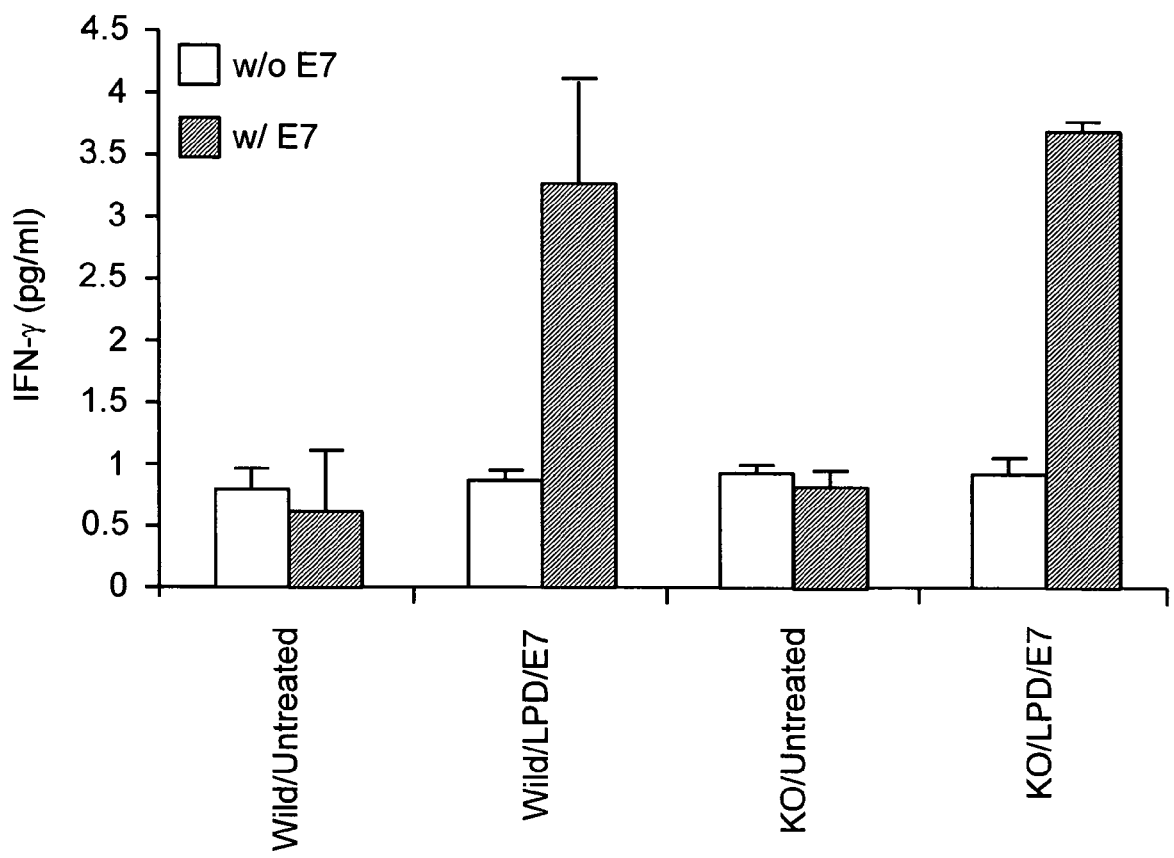
FIG. 4. The role of TLR9 on the antigen specific immune response induced by LPD/E7 nanoparticles. The splenocytes from wild type or TLR9−/− mouse were re-stimulated with 1 μg/ml of E7 peptide for 24 h. The culture supernatants were collected and IFN-α levels were measured using ELISA.

TLR9 is responsible for the action of the immunostimulating unmethylated CpG motifs, e.g., RRCGYY (Hemmi et al., 2000; Bauer et al., 2001). It is a good guess that the adjuvant activity of LPD is mediated by TLR9. To test this hypothesis, we have obtained TLR9 −/− mice (Hemmi et al., 2000) from Professor Shizuo Akira in Japan. The mice are in the background of C57BL/6 and are syngeneic with TC-1 cells. The splenocytes from wild type or TLR9−/− mouse injected with LPD/E7 were re-stimulated with 1 μg/ml E7 peptide for 24 h. The culture supernatants were collected and IFN-γ levels were measured using ELISA. As can be seen in FIG. 4, splenocytes from either wildtype or knockout mice could be stimulated with LPD/E7 to produce IFN-γ to the same extend, indicating that TLR9 is not important in the process of immune stimulation. Again, it suggests that cationic lipid, rather than DNA, was the primary stimulant of the immune system.

Figure 5:
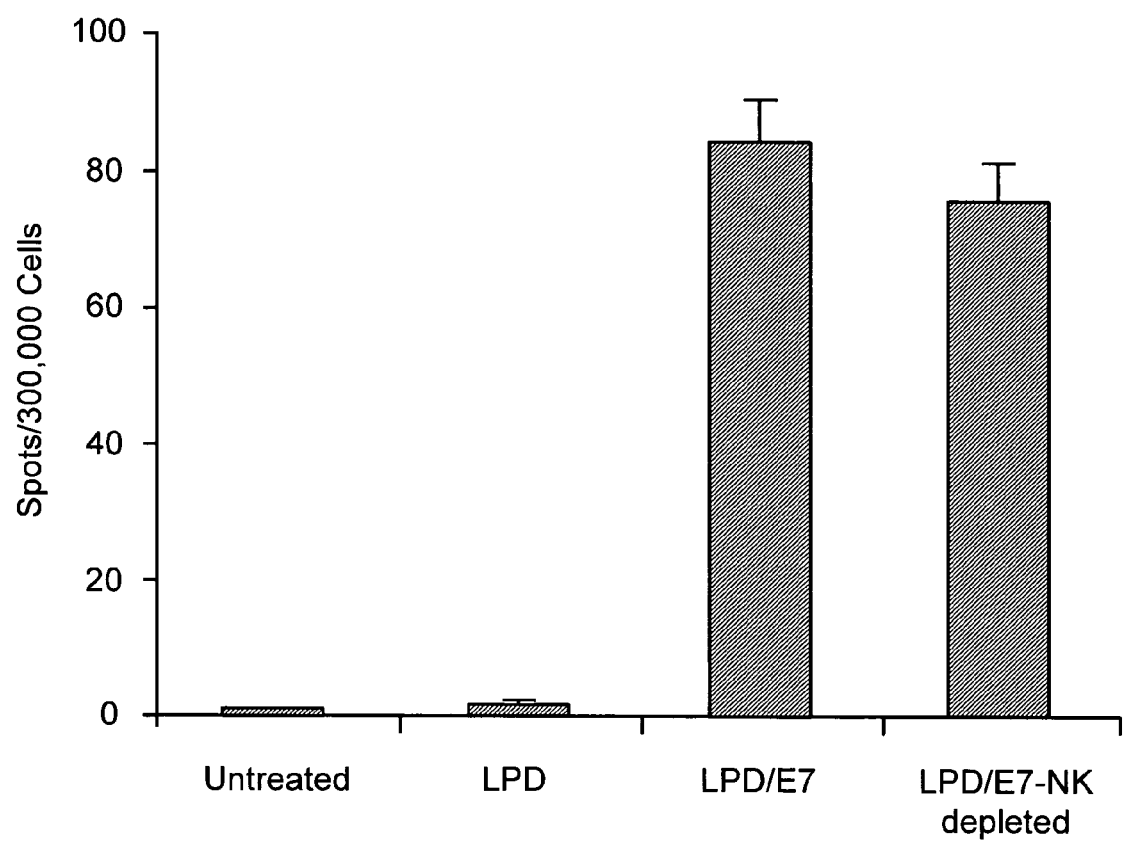
FIG. 5. IFN-γ ELISPOT assay. Mice were s.c. injected with LPD nanoparticles containing 10 μg of E7 peptide or LPD nanoparticles without E7 peptide on day 0 and 5. Five days after the last injection, lymph node cells were isolated, re-stimulated with 1 μg/ml of E7 peptide for 24 h for tumor specific T cell expansion. NK cells were depleted by injection with 100 μg anti-NK1.1 starting 2 days before the first vaccination and ending 2 days after the last vaccination.

According to our preliminary data, approximately 25% of lymphnode NK cells have taken up s.c. injected LPD. Our previous work using LPD without E7 peptide also indicates that NK cells are involved in the first phase of tumor killing, which is followed by induction of tumor specific CTL. Thus, there is a real possibility that NK cells may be activated by LPD and involves in tumor cell killing. To identify whether the NK cells are necessary for the antigen specific immune response, we have eliminated the NK cells by treating the animals with anti-NK1.1 antibody. As can be seen in FIG. 5, the antigen specific T-cell response, measured by IFN-γ ELISPOT assay, was approximately the same as the ones without the NK elimination. This result indicates that NK cells are only important for the antigen independent antitumor activity, but not in the antigen specific activity.

7. Cationic Lipids can Activate Dendritic Cells.

Figure 6:
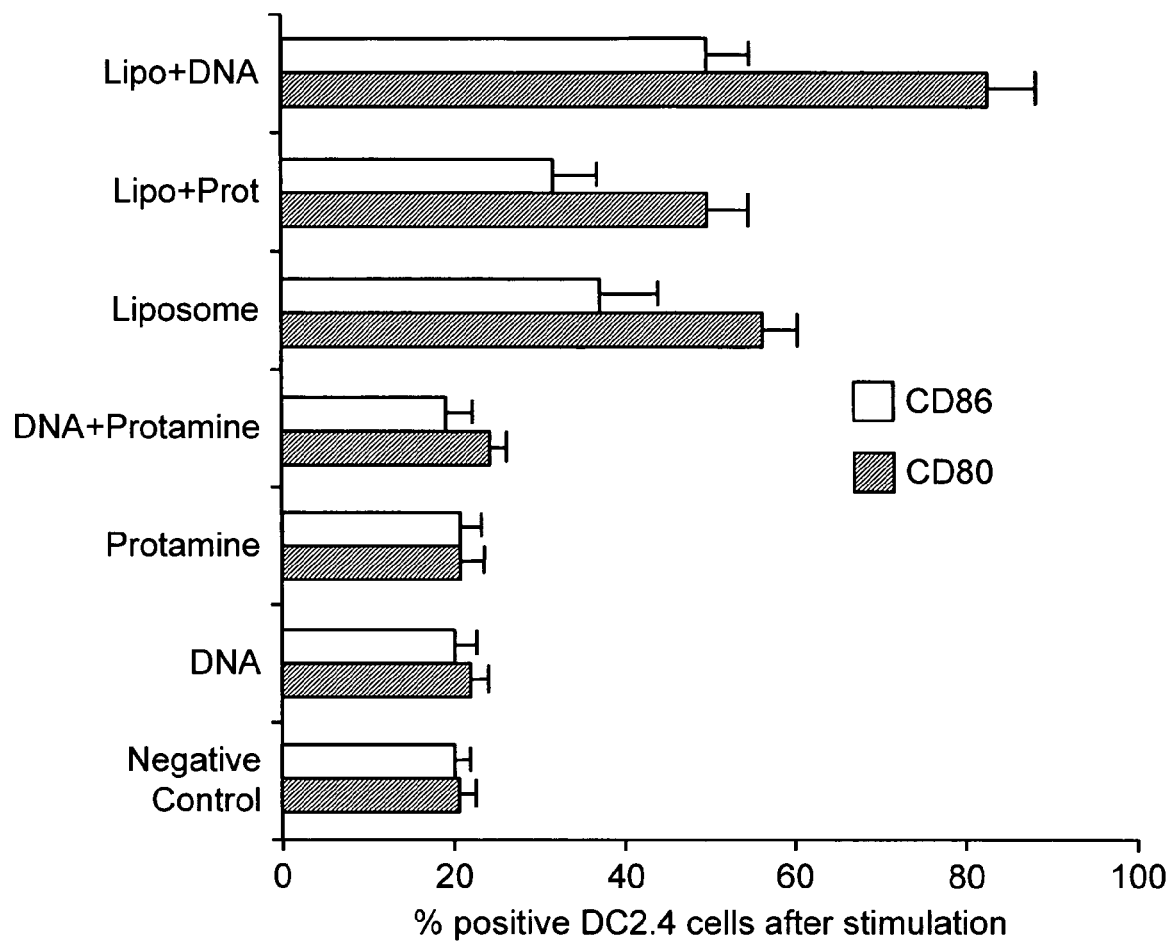
FIG. 6. The expression of co-stimulatory molecules, CD80 and CD86, on DC2.4 cells after stimulation by LPD or the components of LPD.
Figure 7:
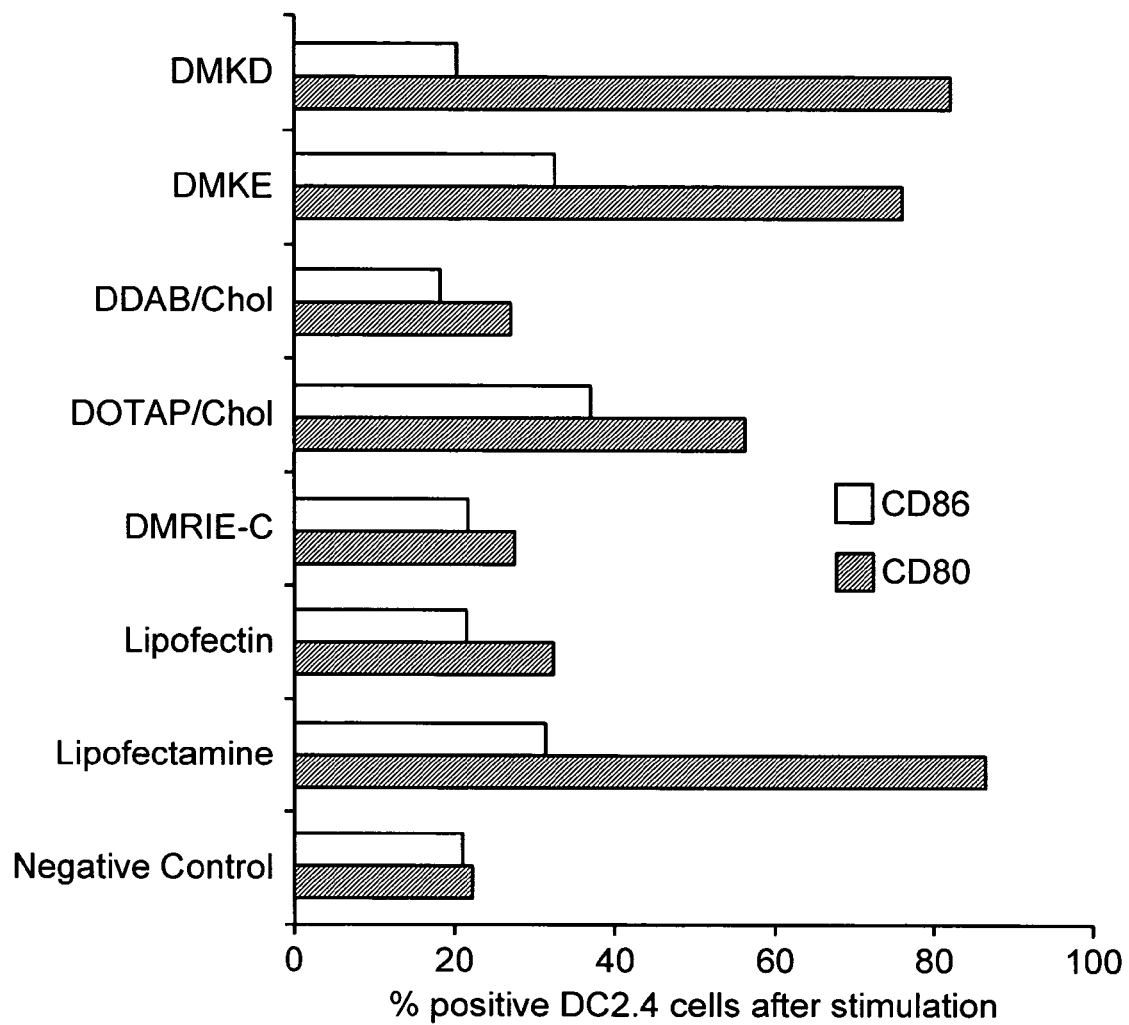
FIG. 7. Expression of co-stimulatory molecules, CD80 and CD86, on DC2.4 cells after stimulation with different cationic liposomes.

Previously we have shown that LPD is a potent vaccine delivery system/adjuvant. Following are some data we collected when studying the mechanism of the strong immunostimulation activity from LPD. We have measured by flow cytometry the expression of co-stimulatory molecules, CD86 and CD80, on DC2.4 cells as the result of stimulation by various components of LPD, including the liposome prepared from cationic lipid 1,2-dioleoyl-3-(trimethylammonium) propane (DOTAP) and cholesterol (Chol), protamine, and DNA. Plasmid DNA alone, protamine alone, and the complex of DNA/protamine did not stimulate the expression of CD80/CD86 (FIG. 6). LPD stimulated DC2.4 cells expressed the highest amount of CD80/CD86. Lipoplex prepared from liposome (DOTAP/Chol) and DNA was as effective as the LPD, indicating that protamine is not required for DC cell stimulation. In addition, cholesterol is not required for DC cell stimulation (FIG. 6) since LPD prepared from liposomes comprised of DOTAP alone is as effective as those prepared from liposomes comprised of DOTAP and cholesterol. Finally, it was found that CD80/CD86 expressions from liposome alone (DOTAP/Chol) stimulated DC2.4 cells were up to 70% of that from LPD stimulated DC2.4 cells, strongly demonstrating that the DOTAP-based cationic liposome alone can activate DCs and is responsible for the some of the LPD adjuvant activity. Therefore, a few other cationic liposomes were also tested for their ability to stimulate the expression of CD80/CD86 by DC2.4 cells. To our surprise, as shown in FIG. 7, the ability to stimulate the expression of CD80/CD86 on DC2.4 cells by different cationic liposomes varies greatly. Lipofectamine®, a 3:1 (w/w) liposome formulation of the polycationic lipid 2,3-dioleyloxy-N-[2(sperminecarboxamido) ethyl]-N,N-dimethyl-1-propanaminium trifluoroacetate (DOSPA) and the neutral lipid dioleoyl phosphatidylethanolamine (DOPE), and liposomes prepared from O,O'-dimyristyl-N-lysyl aspartate (DMKE) and O,O'-dimyristyl-N-lysyl-glutamate (DMKD), two newly synthesized cationic lipids by Dr. Yong-Serk Park, strongly stimulated the expression of CD80/CD86 by CD2.4 cells, whereas Lipofectin®, a 1:1 (w/w) liposome formulation of cationic lipid N-[1-(2,3-dioleyloxy)propyl]-n,n,n-trimethylammonium chloride (DOTMA) and DOPE, DMRIE-C®, a 1:1 (M/M) liposome formulation of cationic lipid 1,2-dimyristyloxypropyl-3-dimethyl-hydroxy ethyl ammonium bromide (DMRIE) and cholesterol, and liposome prepared from cationic lipid dimethyldioctadecylammonium bromide (DDAB) and cholesterol did not show any significant stimulation on the expression of CD80/CD86 by DC2.4 cells.

Figure 8:
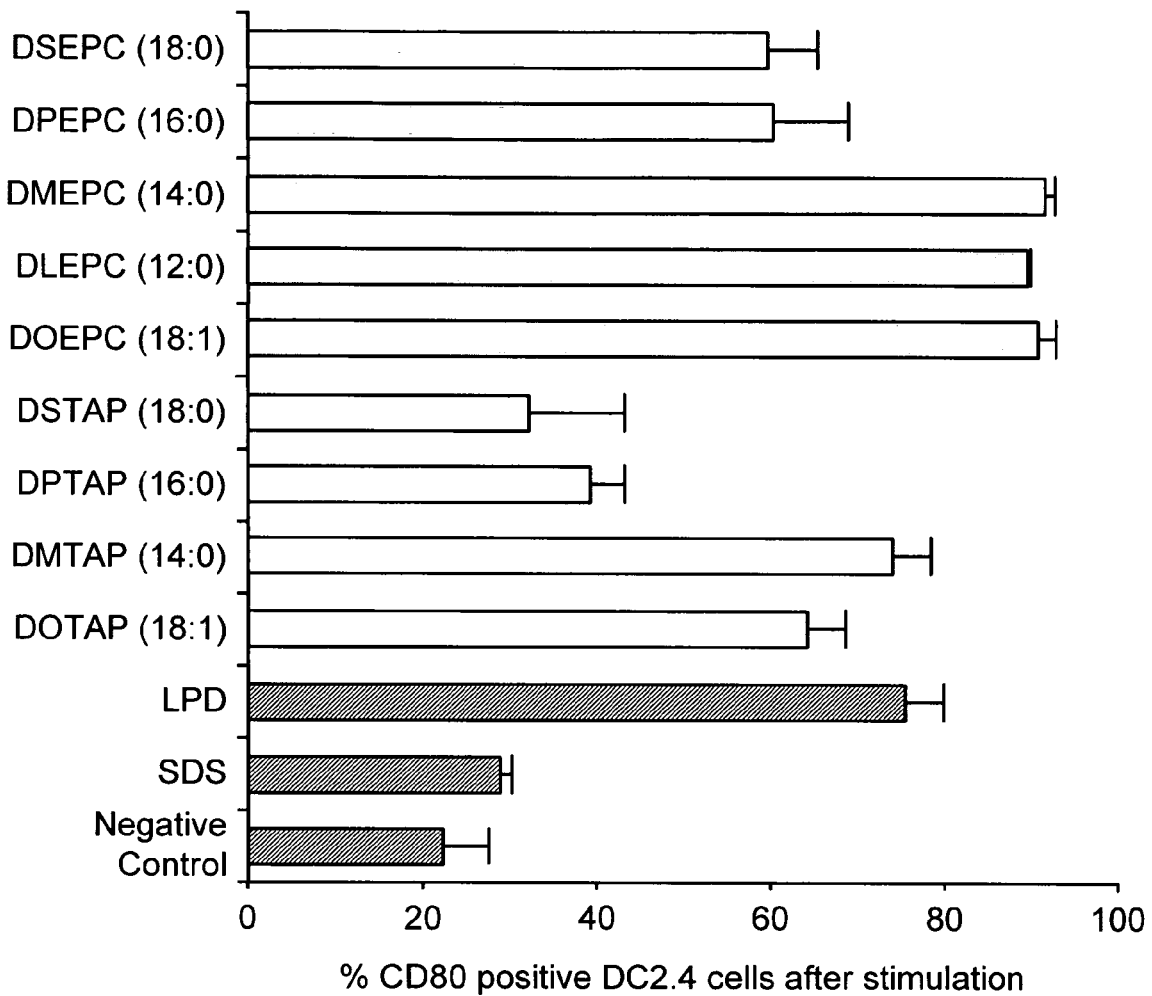
FIG. 8. Hydrocarbon chain length dependence of cationic lipids on the expression of co-stimulatory molecule (CD 80) on DC 2.4 cells.

The ability of different cationic lipids to stimulate the expression of CD 80 on DC 2.4 cells varied significantly. Both hydrophilic head and the lipophilic tail of the lipids have significant effect on this ability. For example, the DXEPC lipids with the ethyl phosphocholine (EPC) head groups are, in general, more potent than the DXTAP lipids with trimethylammonium propane (TAP) head group. The effect of the hydrocarbon tail region of the lipids on the DC cell stimulation also was systematically investigated (FIG. 8). Within the lipids bearing one particular head group structure, lipids with shorter (1,2-dilauroyl-sn-glycero-3-ethylphosphocholine (DLEPC-12:0), 1,2-dimyristoyl-sn-glycero-3-ethylphosphocholine (DMEPC-14:0)) or unsaturated (1,2-dioleoyl-sn-glycero-3-ethylphosphocholine (DOEPC-18:1)) acyl chains are found to be more potent than those with longer (1,2-dipalmitoyl-sn-glycero-3-ethylphosphocholine (DPEPC-16:0)) or saturated (1,2-distearoyl-sn-glycero-3-ethylphosphocholine (DSEPC-16:0)) acyl chains. Similar trends were observed with lipids having TAP head groups also with 1,2-distearoyl-3-trimethylammonium propane (DSTAP-18:0) and 1,2-palmitoyl-3-trimethylammonium propane (DPTAP-16:0) showing much lower expression of CD80 on DC 2.4 cells compared to that of 1,2-myristoyl-3-trimethylammonium propane (DMTAP-14:0) and 1,2-oleoyl-3-trimethylammonium propane (DOTAP-18:1). Detergent sodium dodecyl sulfate (SDS) could not activate DC 2.4 cells for the expression of CD 80 suggesting that the DC 2.4 activation by cationic lipids with shorter hydrophobic chains were not due the possible detergent effect of shorter chain lipids on the cell membrane.

Figure 9:
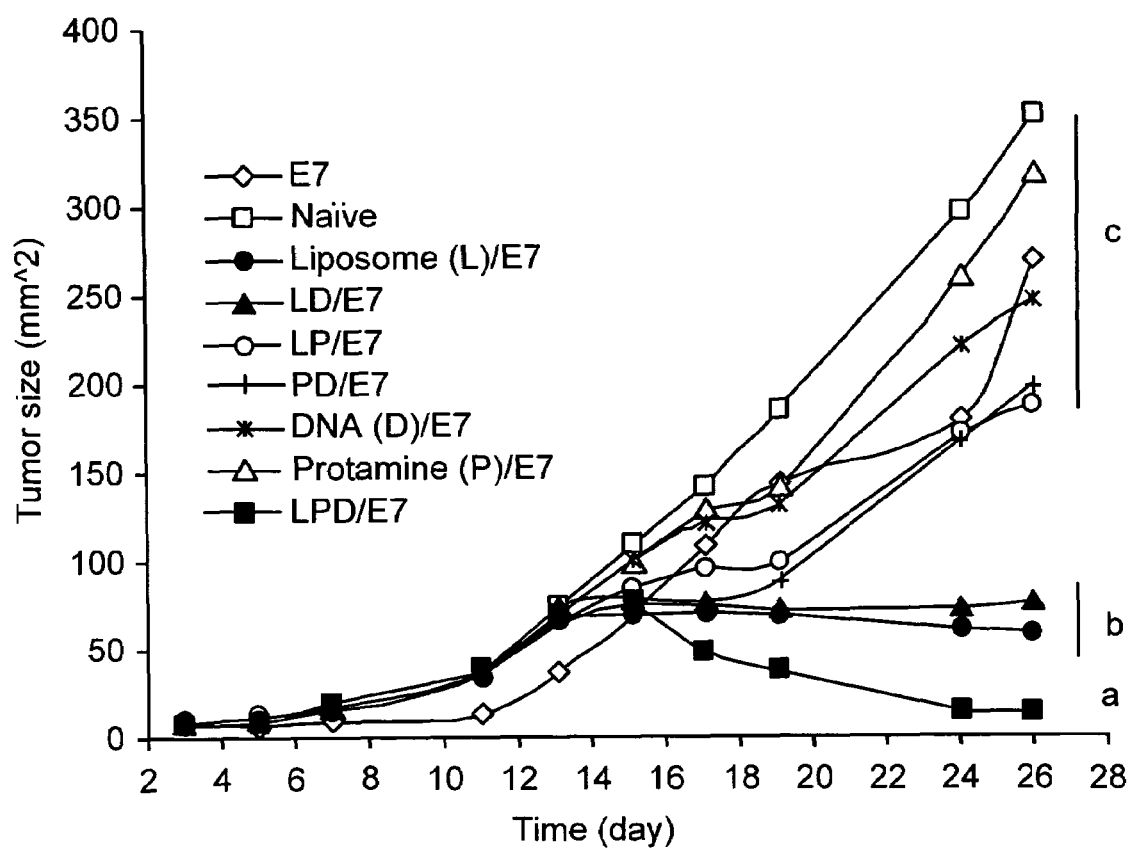
FIG. 9. Tumor growth kinetics on mice treated with LPD/E7 and other different formulations. The letters a, b, and c indicate that the final mean tumor sizes were significantly different between the groups, but not different within the group.

To further prove that both DNA and cationic liposome are required for the full activity of LPD, an in vivo tumor therapy study was carried out. As shown in FIG. 9, 20 days after treatment with E7 peptide-incorporated LPD (LPD/E7), the tumor (injected 6 days before the onset of treatment) almost totally regressed. Liposome/E7 and lipoplex/E7 (LD/E7) showed effect to some extent but significantly weaker than that of the LPD/E7. Tumors in mice treated with other formulations including DNA/E7, protamine/E7, LP/E7, PD/E7, and E7 alone kept growing rapidly with the final tumor size comparable to those on the untreated naïve mice. Therefore, the result of this tumor therapy study again demonstrated that both DNA and cationic liposome are required for the full immunostimulation activity of LPD. It is interesting to note that in the tumor model, protamine becomes functionally important, as the activity of LPE/E7 was significantly greater than that of LD/E7. It is speculated that by condensing DNA, protamine helped to bring DNA inside the liposomes. E7 peptide was thought to bind to DNA via electrostatic interaction (Dileo et al., 2003). In LPD/E7, the E7 peptide might locate inside the liposome and should be protected from enzymatic degradation after injection. On the other hand, E7might only be loosely bound in the LD/E7 particles. In fact, the peptide incorporation efficiency of LPD/E7 was ~80%, whereas for LD/E7 and L/E7, it was about 65%.

8. Genetically Engineered HPV 16 E7 Protein as a Potential Cervical Cancer Vaccine.

Previously, we showed that a seven amino acid peptide from HPV 16 E7 protein, when incorporated into LPD nanoparticles, induced strong anti-tumor response the can prevent and treat tumors grafted on mice. In the present study, we hypothesized that the LPD particles could also be used as a carrier for E7 protein to induce strong antibody and anti-tumor responses. We also hypothesized that by introducing mutations on E7 protein, we can delete the oncogenic activity of E7 but keep its antigenic activity.

Figure 10:
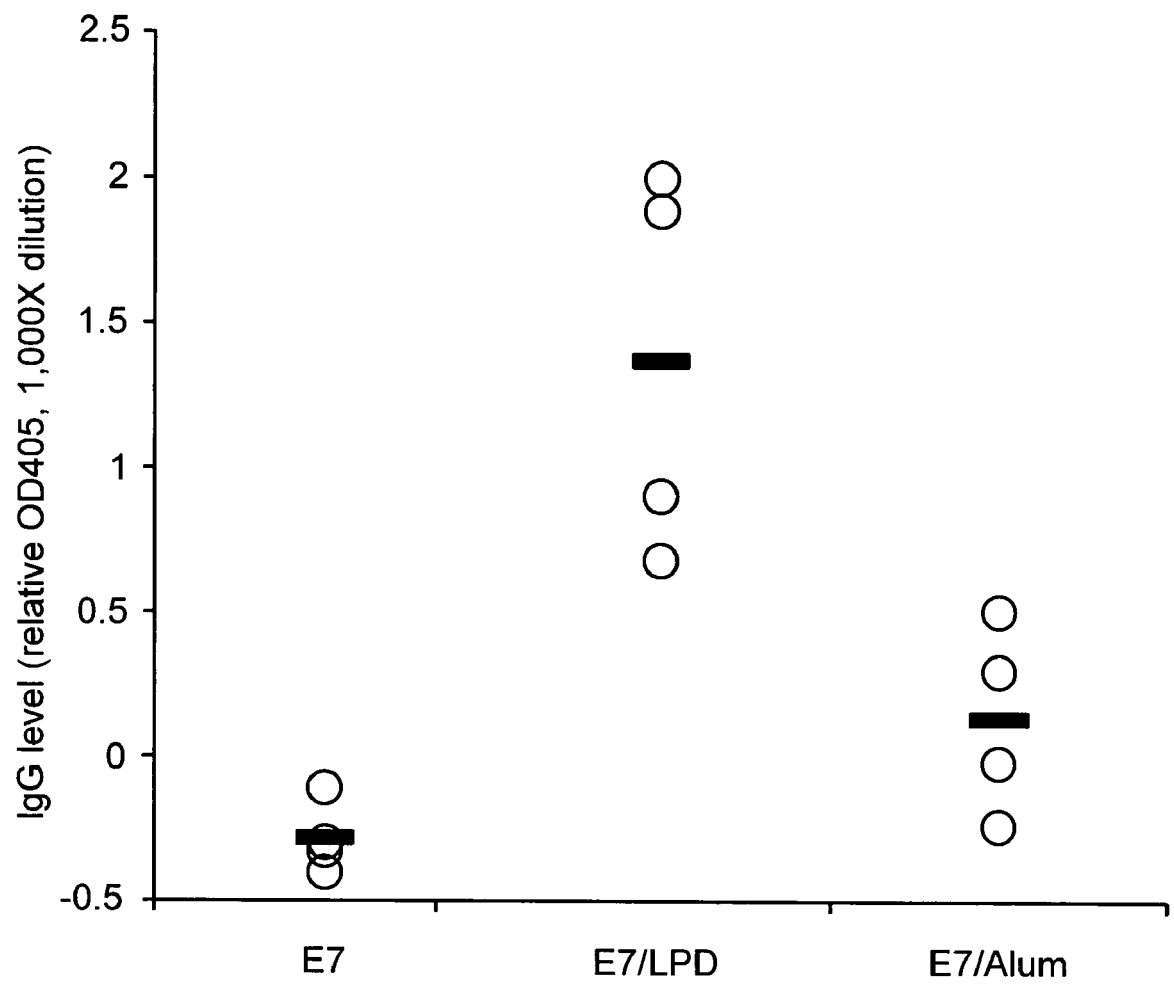
FIG. 10. Specific IgG level in serum after diluted for 1,000-fold. Mice (n=4-5) were immunized with E7 protein alone, E7/LPD, and E7 adjuvanted with 'Alum' (15 μg/mouse) (E7/Alum). The dose of E7 protein was 20 μg/mouse. As control, one group of mice was left untreated. Mice were immunized on day 0 and 14. On day 28, mice were bled via tail vein. ANOVA analysis on the three treatments showed a p value of 0.001. * indicates that the value from E7/LPD is significantly different from that of the others.
Figure 11:
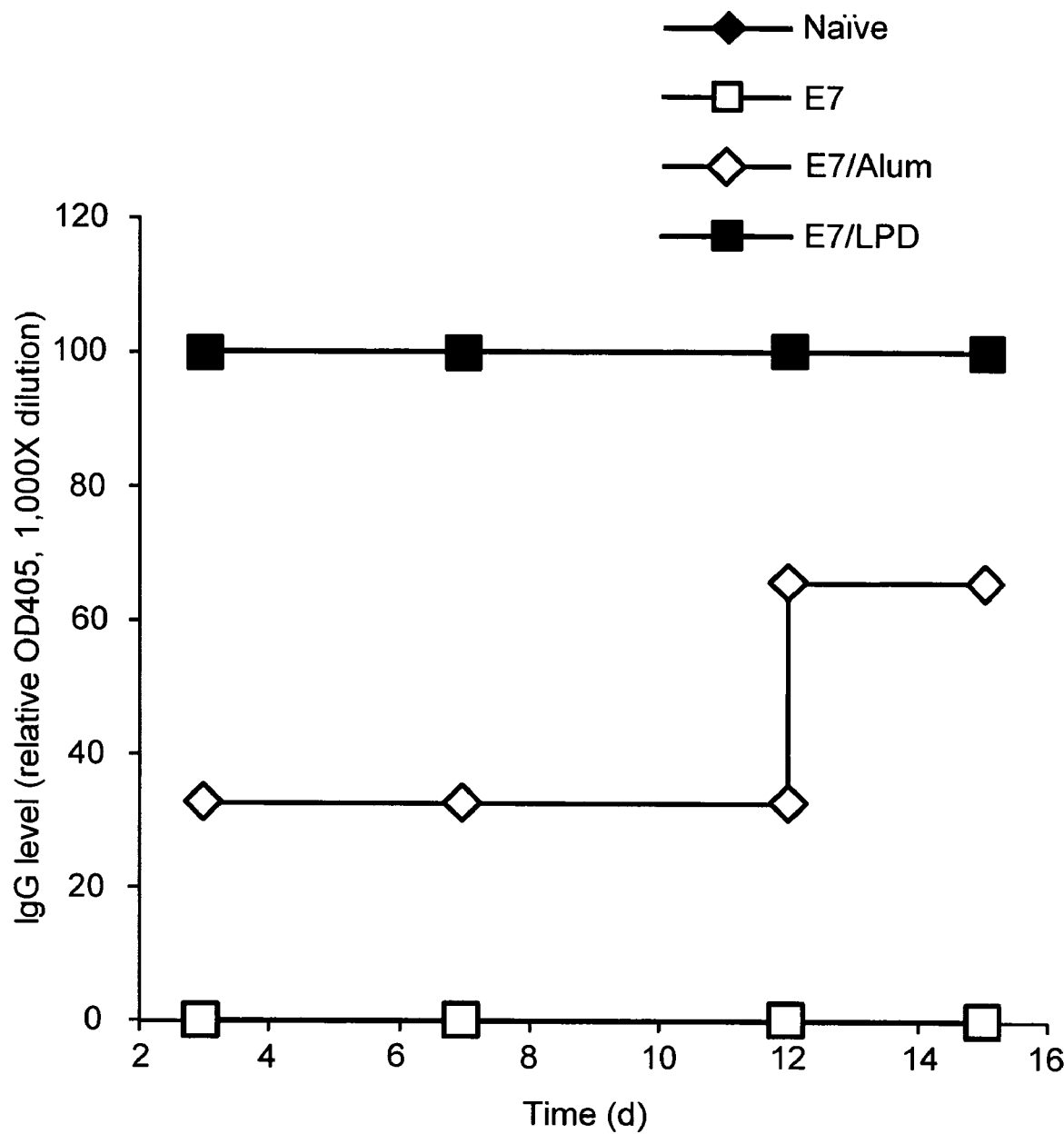
FIG. 11. Immunization with E7/LPD prevented TC-1 tumor cell growth in C57BL/6 mice (n=6). Mice were immunized on day 0 and 14 as in FIG. 1. On day 21, TC-1 cells ($5 \times 10^5$) were injected subcutaneously. The growth of the tumors was monitored for 15 days. Showing is % of tumor free mice as a function of time. Statistic analysis showed that, the line for E7/Alum is different from that for E7/LPD (p=0.02).
Figure 12:
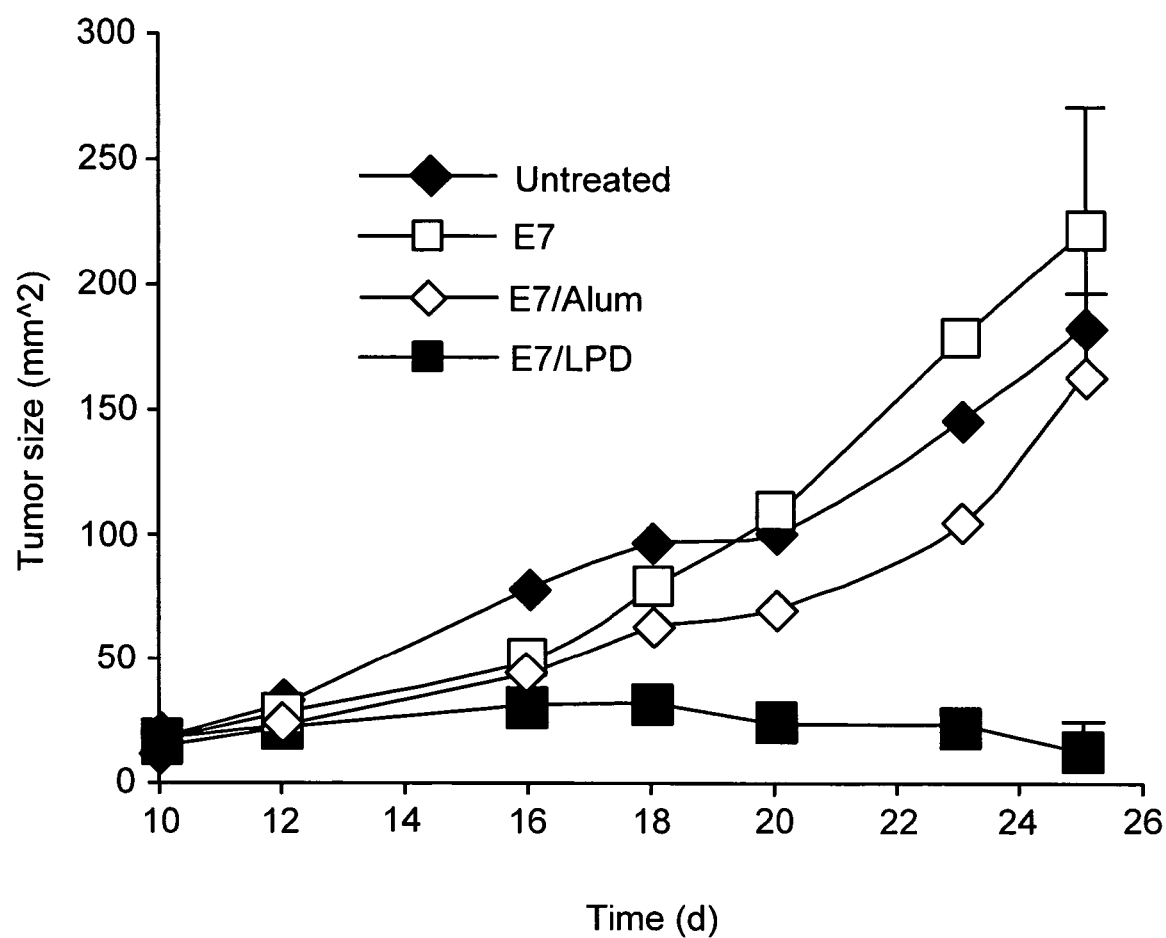
FIG. 12. Treatment with E7/LPD caused regression of tumors. Mice (n=5) were subcutaneously injected with TC-1 cells ($5 \times 10^5$/mouse) on day 0. On day 4, they were treated with E7 alone, E7/LPD, or E7/Alum. Dosage is same as in FIG. 1. Showed is the tumor growth kinetics. On day 25, the tumor size from E7/LPD treated mice is significantly smaller than that from other treatments (p=$5 \times 10^{-6}$, ANOVA).

To investigate whether strong immune responses can be elicited when E7 protein is incorporated into LPD nanoparticles as a vaccine, E7 protein was expressed in *E. coli*, purifed, detoxified, and incorporated into LPD particles. E7/LPD was then used to immunize C57BL/6 mice. The resulting antibody, tumor prevention, and tumor treatment activity from E7/LPD were compared to that of E7 alone or E7 adjuvanted with 'Alum'. Data showed that E7/LPD induced antibody level (specific IgG) significantly higher than that of E7/Alum (FIG. 10). Also, E7/LPD immunization prevented the growth of TC-1 tumor cells on mice (FIG. 11); visible tumor (4 day old) on mice totally regressed when the mice were treated with E7/LPD (FIG. 12).

To engineer the E7 protein to delete its oncogenic activity, and hopefully, without disrupting its immunogenicity, the following experiments were carried out. For the engineering of mutated E7 protein, an overlapping PCR was used. Amino acids D21 and C94 on E7 protein were changed to G21 and G94 by changing their codons from GAT to GGT and TGT to GGT, respectively. The four primers used were P1, 5'-TTGGGATCCACCATGCATGGAGATACAC-CTAC-3' (SEQ ID NO:1); P2, 5'-CGGAATTCATTCT-TATGGTTTCTGAGAACCGATGGGGCACACA-3' (SEQ ID NO:2); P3, 5'-GAGACAACTGGTCTCTACTGTTAT-3' (SEQ ID NO:3); and P4, 5'-ACAGTAGAGACCAGT-TGTCTCTGG-3' (SEQ ID NO:4). Using pET-E7 as the template, two separate PCRs were completed using primer P1/P4 and P2/P3 as the primer pairs, respectively. The PCR products were purified using QiaQuick® PCR purification Kit (Valencia, Calif.). Another PCR was completed using P1 and P2 as the primers and equal molar of the products from the two previous PCRs as the templates. The PCR conditions were 94° C. for 5 min followed by 35 cycles of 94° C., 0.5 min, 56° C., 1 min, and 72° C., 0.5 min. Another 5 min of incubation at 72° C. was included prior to the end of the PCR reaction. Taq DNA polymerase and dNTP were from Promega (Madision, Wis.). After purification, the PCR product was then ligated to the pGEM®-T vector from Promega. The ligation reaction was then transferred into E. coli DH5a strain. Positive colonies were selected using LB/ampicillin/IPTG/X-Gal plates. After confirmation of mutations on the E7 gene of the pGEM®-T-E7m, the plasmid was digested with BamH1 and EcoR1, whose restriction sites are on primer P1 and P2, respectively. The resulting DNA fragment was gel purified and then cloned into the BamH1 and EcoR1 site of pCDNA3.1(+) vector (Invitrogen, Carlsbad, Calif.) and pET vector (Novagen, Madison, Wis.), respectively. The plasmid constructs were transferred into E. coli DH5a and selected against ampicillin and kanamycin, respectively.

Figure 13:
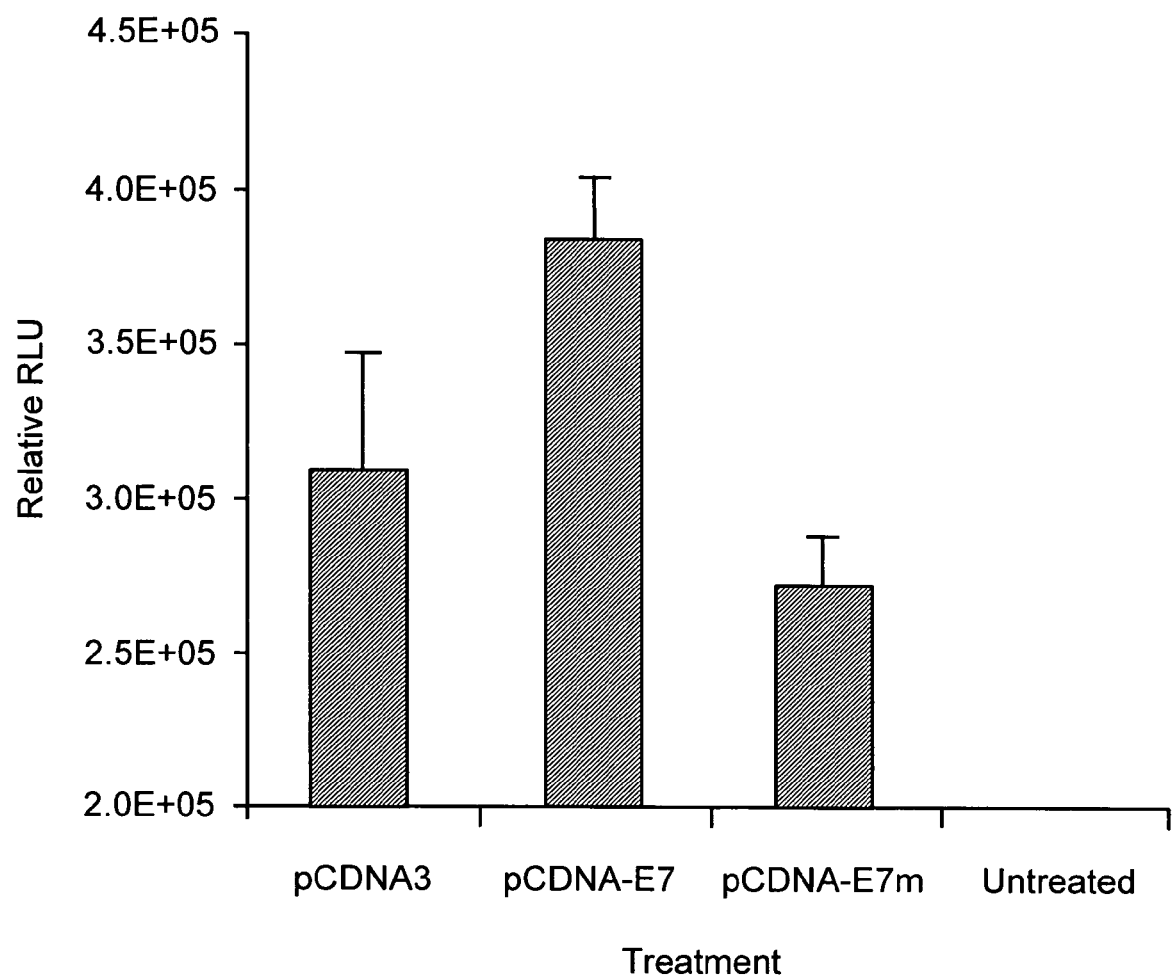
FIG. 13. Relative RLU in 293 cells transfected with a CMV driven β-galactosidase gene containing plasmid, cdc25A Sac1-luc, and pCDNA3(+) with or without E7/E7m gene. * indicates that the value for pCDNA-E7 is different from that of the others (p=0.002, ANOVA). Also, the value for pCDNA3 is not different from that for pCDNA-E7m (p=0.19).

An indirect method was used to verify that E7m lost its ability to bind to pRB protein and therefore is unable to activated E2F driven genes. E7 and E7m genes were inserted into the BamH1 and EcoR1 sites of pCDNA3.1(+) vector. The resulting plasmids were amplified in E. coli DH5a strain and purified. Plasmid cdc25A Sac1-luc, in which luciferase gene is driven by a 1173 (−755 to +418) bp Sac1 fragment of the cdc25A promoter, is a gift from Dr. D. DiMaio from Yale University (New Haven, Conn.). The SacI fragment has both HPV 16 E2 protein binding site and the E2F binding site. Plasmid cdc25A SacI-luc, pCDNA3.1 (+) with or without E7 or E7m insert, and a CMV driven β-galactosidase gene containing plasmid were cotransfected into confluent 293 cells ($5\times10^5$/well, incubated at 37° C. and 5% $CO_2$ overnight, DMEM medium with 10% FBS) with Lipofectamine® (Invitrogen). The plasmid ratio was 2:1:10 (w/w/w) with pCDNA3.1(+) plasmid at 1 µg/well. Four hours after the addition of the plasmids, the medium was replaced with fresh medium. After another 44 h, the incubation was stopped. Cells were washed with cold PBS (10 mM, pH 7.4) for twice and lysed. Luciferase activity, β-galactosidase expression, and total protein amount were then determined. Relative light unit normalized to galactosidase protein level and total protein amount was reported. As shown in FIG. 13, when 293 cells were co-transfected with E2F responsive element driven luciferase gene encoding plasmid (cdc25A Sac I-luc) and an E7 protein encoding plasmid (pCDNA-E7), significantly higher luciferase expression was observed than when cdc25A Sac I-luc was co-transfected with an empty plasmid (pCDNA3) (p=0.02). However, when pCDNA-E7m was cotransfected with cdc25A Sac I-luc, the resulting luciferase level was comparable to that when cdc25A Sac I-luc and pCDNA3 were co-transfected (p=0.19). Taken together, these date suggest that the mutations on E7m may abolish its ability to bind to pRB and thus the oncogenic activity.

Figure 14:
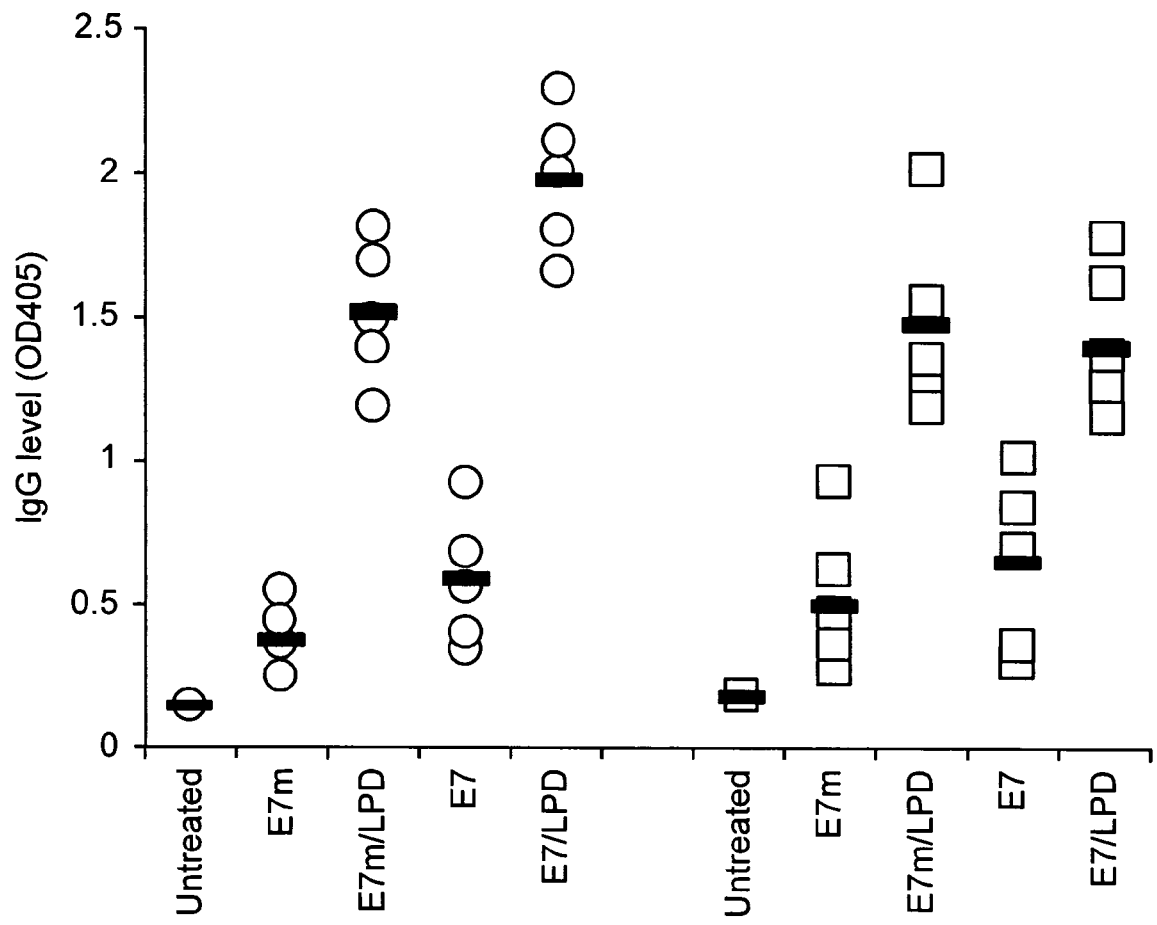
FIG. 14. Specific IgG levels in mice immunized with E7m, E7m/LPD, E7, and E7/LPD. Mice (n=5-6) were immunized on day 0 and 14. Shown are IgG levels in serum on day 28 (○) and 60 (□). The IgG levels from E7 or E7m alone immunized mice were significantly lower than those from E7/LPD or E7m/LPD immunized mice. On day 28, the value for E7m/LPD is lower than that for E7/LPD (p=0.02); on day 60, the values from these two treatments are similar (p=0.53). For E7m/LPD, the value from day 28 is similar to that from day 60 (p=0.81); for E7/LPD, these two values are different (p=0.004).

To investigate whether the mutations introduced on E7 affect the mutated protein's ability to induce antibody and antitumor responses, E7 and E7m proteins were purified and used to immunize mice. The resulting specific antibody levels and tumor treatment abilities were compared. Shown in FIG. 14 are the specific antibody levels in serum on day 27 and day 60. Again, both E7/LPD and E7m/LPD induced significantly higher IgG level than E7 and E7m alone without LPD. Interestingly, on day 27, the IgG level from E7/LPD was higher than that from E7m/LPD (p=0.019); whereas on day 60, the IgG level from E7/LPD was comparable to that for E7m/LPD (p=0.53). This is due to the significant decreased IgG level in E7/LPD immunized mice as time passed (p=0.004). The above data are the antibody levels when measured against E7 protein as an antigen. Similar results were obtained when measured against E7m protein.

Figure 15:
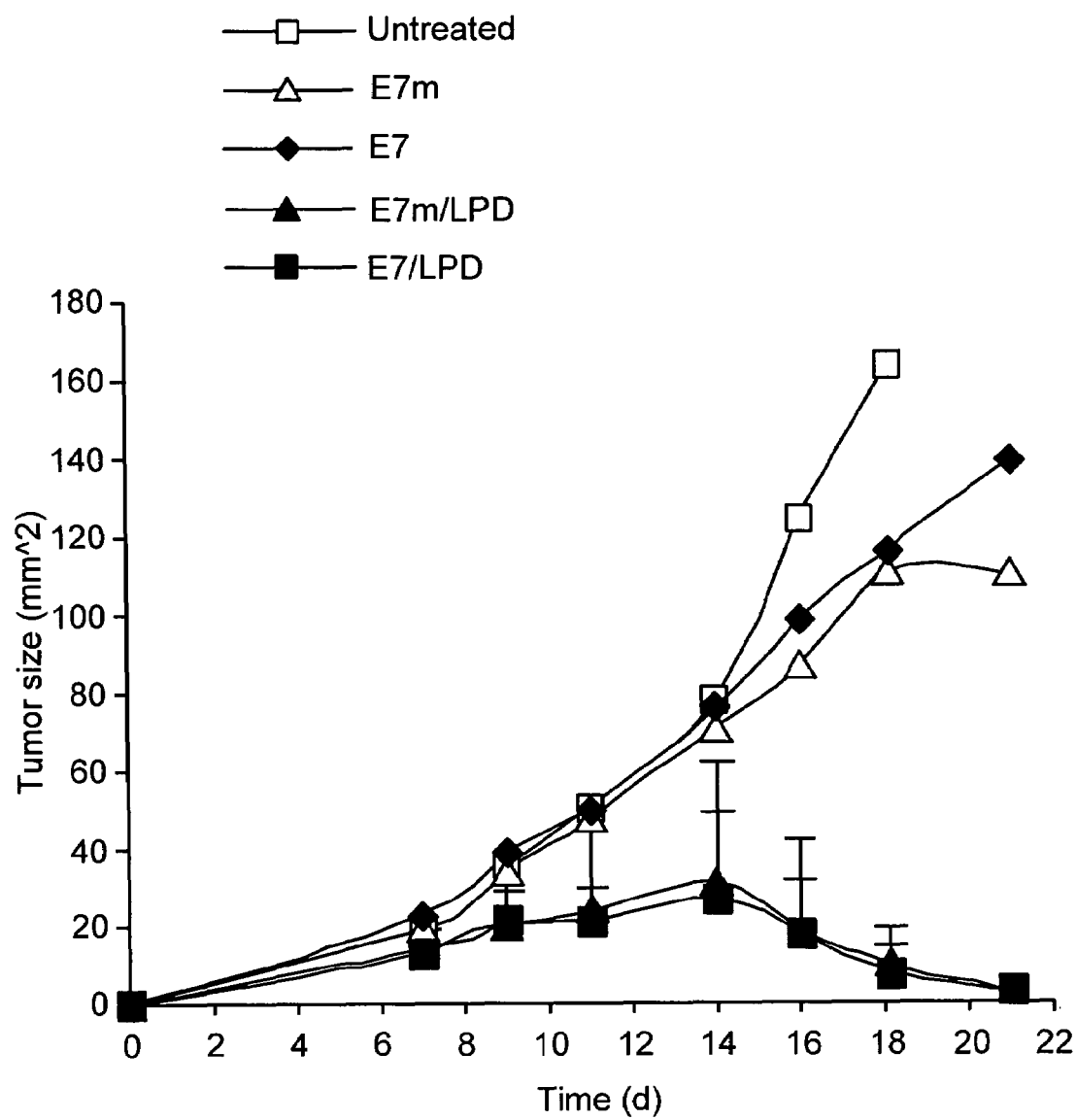
FIG. 15. E7m/LPD and E7/LPD are equally effective in treating tumor. Mice (n=5 or 10, 10 for E7/LPD and E7m/

Treatment of tumor bearing mice with E7m/LPD is as effective as with E7/LPD in causing tumor regression (FIG. 15).

In summary, mutations in the E7 protein have been successfully introduced. The resulting mutated E7m protein losses its oncogenic property, but is as immunogenic as the original E7 protein.

EXAMPLE II

LPD Mediated Antigen Delivery to Antigen Presenting Cells Results in Enhanced Anti-Tumor Immune Response A. Materials and Methods 1. DNA, Cell Lines and Peptides TC-1 cells were provided by TC Wu (Johns Hopkins University, Baltimore, Md.). These cells are C57BL6 mouse lung endothelial cells that have been transformed with the HPV16 E6 and E7 oncogenes and activated H-ras. Cells were grown in RPMI medium (Invitrogen, Carlsbad, Calif.) supplemented with 10% fetal bovine serum and 100 U/ml penicillin, and 100 mg/ml streptomycin. Cy3 labeled phophodiester oligodeoxynucleotides were purchased form Invitrogen (Carlsbad, Calif.). pNGVL3 was obtained from the National Gene Vector Laboratory (University of Michigan) and contains the CMVie promoter and no coding region. Plasmids were prepared using Qiagen EndoFree Giga-Prep kits (Qiagen, Valencia, Calif.). The MHC class I restricted peptide from the HPV 16 E7 protein (aa 49 to 57, RAHYNIVTF; SEQ ID NO:5) was synthesized by the University of Pittsburgh Peptide Synthesis Facility by solid state synthesis using an Advanced ChemTech model 200 peptide synthesizer and purified by HPLC. (Feltkamp, et al. *Eur J Immunol* 23, 2242-2249 (1993)).

2. Liposome and LPD Preparation

All lipids were purchased from Avanti Polar Lipids (Alabaster AL). Small unilamellar DOTAP (1,2-Dioleoyl-3-Trimethylammonium-Propane):cholesterol (1:1 molar ratio) liposomes were prepared by thin film hydration followed by extrusion. LPD complexes were prepared using the procedure described by Li with modifications (Li, et al. *Gene Ther* 5, 930-937 (1998)). Briefly, complexes contained an 8.5:0.6:1.0 weight ratio of DOTAP/cholesterol liposomes:protamine:DNA. Liposomes and protamine (Sigma, St Louis Mo.) were mixed in 75 µl of 5.2% dextrose solution. 75 µl of a solution containing plasmid DNA and E7 peptide was slowly added by dropwise addition with constant mixing. Complexes were incubated for 20 min at room temperature prior to injection. LPD/E7 particle size was determined by dynamic light scattering using a Coulter N4 plus (Beckman Coulter, San Francisco) and found to be indistinguishable from LPD particles (110±30 nm and 123±40 nm, respectively n=3). Peptide encapsulation efficiency was determined using FITC-labeled E7 peptide and was found to be 83±4% (n=3).

Sterically stabilized liposomes (SL liposomes) were prepared according to Ignatius et al (29). Briefly, small unilamellar cholesterol:Palmitoyl-Oleoyl Phosphatidylcholine (POPC):PEG-PE (2:3:0.3 molar ratio) liposomes were prepared by thin film hydration with a 1 mg/ml E7 peptide containing solution followed by extrusion.

3. Immunizations/Treatments

Six-week-old female C57BL/6 mice (Charles River Labs, Wilmington, Mass.) were used in all experiments. For vaccinations, mice were injected through the tail vein or subcutaneously with LPD particles containing 25 µg of pNGVL3 (University of Michigan) and 20 µg of E7 peptide on days 0 and 5. On day 10, mice were challenged by SC injection of $0.5 \times 10^6$ TC-1 cells and mice were observed for the formation of tumors by palpation twice per week.

For therapy experiments, SC tumors were established by injecting $0.5 \times 10^6$ TC-1 cells on day 0. Mice were IV injected with LPD complexes 3 and 6 days later as described in the text. Tumor size was monitored twice per week and size was determined by multiplying the two largest dimensions of the tumor. In some cases, mice were anesthetized and spleens were surgically removed 10 days prior to tumor inoculation.

4. CTL Assays

Cytolytic lymphocyte activity was measured using standard $^{51}$Cr-release assays. Splenocytes were collected and cultured in RPMI supplemented with 10% FBS, 50 U/ml penicillin/streptomycin, 2 mM L-glutamine, 1 mM sodium pyruvate, 2 mM nonessential amino acids, 40 U/ml IL2, and 200 ng/ml MHC class I restricted E7 peptide for 4 days. Effector cells were plated into 96-well plates at various effector-to-target (E:T) cell ratios. Targets used were either EL4 cells pulsed with E7 peptide or non-pulsed EL4 cells. Targets were labeled with 200 µCi $^{51}$Cr (NEN Life Sciences, Boston Mass.) for 18 h at 37° C. Before mixing with effectors, the targets were washed two times with medium, and resuspended at $2 \times 10^5$ cells/ml. The lysis reaction was carried out for 4 h at 37° C., after which the plates were centrifuged, and 100 µl of medium from each well were assayed for $^{51}$Cr content in a scintillation counter. Specific lysis was calculated using the following equation:

% specific lysis=(experimental release–spontaneous release)/(maximum release–spontaneous release)×100.

5. Histology

To visualize LPD distribution, mice were injected with LPD particles containing 25 µg pNGVL3, 0.1 µg Cy3 labeled oligodeoxynucleotides (ODN) and 10 µg E7 peptide in 150 µl 5% dextrose. 12, 24, and 48 h later, spleens were collected, embedded in OCT medium, frozen, and 6 µm sections were prepared and observed at 200× magnification using a Nikon Eclipse TE300 inverted fluorescent microscope and SPOT image analysis software.

6. Flow Cytometry

Phycoerythrin (PE) conjugated antibodies were purchased from BD Pharmingen (San Diego Calif.). Spleens were collected 12, 24, and 48 h after administration of LPD containing fluorescein (FITC) labeled ODN. Single cell suspensions were prepared and stained for CD11b or CD11c using the M1/70 and HL3 antibodies respectively. Samples were run on an EPICS-XL benchtop cytometer (Beckman-Coulter, San Francisco) and analyzed using EXPO 32 software.

B. Results

1. LPD/Peptide Complexes Accumulate in the Spleen and are Taken up by APCs

As delivery to organized lymph tissue is important for successful vaccination, we wished to visualize the distribution of LPD particles within the spleen. To this end, C57BL6 mice were IV injected with LPD/E7 particles containing trace amounts of Cy3-labeled DNA. At 12, 24, and 48 h after injection, spleens were collected, sectioned and the distribution of fluorescence was observed. Mice injected with non-fluorescent LPD particles served as controls. After IV administration, LPD particles rapidly accumulate in the marginal zones of the spleen. (FIG. 16) At 24 h, the majority of the fluorescence was still located in the marginal zones but began to be seen in the white pulp. By 48 h, fluorescence was less intense and was found in a diffuse pattern. Control mice showed no fluorescence.

To determine if LPD/E7 particles are taken up by antigen presenting cells, C57BL6 mice were IV injected with LPD/E7 particles containing trace amounts of FITC-labeled DNA. At 12, 24, and 48 h after injection, splenocytes were collected, stained for CD11c (to identify dendritic cells) and CD11b (to identify macrophages and myeloid lineage DCs), using PE-labeled antibodies and subjected to flow cytometric analysis (FIG. 17). Mice injected with non-fluorescent LPD particles served as control. At 24 h, 3.9% of total splenocytes were CD11b/DNA double positive and 1.7% were CD11c/DNA positive (FIG. 17A). However, these numbers represent approximately 18% (3.9% of 21.6%) and 30% (1.7% of 5.7%) of all CD11b and CD11c positive cells respectively (FIG. 17B). Similar percentages were observed at 12 and 48 h. Control mice and splenocytes stained with isotype control antibodies showed <0.5% positive cells for both CD11b and CD11c.

2. LPD/E7 Complexes Induce an E7 Specific Immune Response

Previous work has shown that the induction of E7 specific CTL activity is important for tumor control (Cheng, et al. *J Clin Invest* 108, 669-678 (2001); and Cheng, et al. *J Virol* 75, 2368-2376 (2001)). To determine if LPD/E7 particles induces significant CTL activity, mice were SC or IV vaccinated with LPD particles containing 0, 1, 10, or 20 µg of E7 peptide on days 0 and 5. For comparison, mice were injected with 20 µg E7 peptide in PBS or encapsulated in stabilized liposomes (SL liposomes). Five days after the final vaccination, splenocytes were collected, and used as effector cells in a chromium release assay. Consistent with previous reports, antigen containing SL liposomes induced significant levels of CTL activity (61% specific lysis) following SC injection only (FIG. 18) (Ignatius, et al. *Blood* 96, 3505-3513 (2000)). Vaccination with 20 µg LPD/E7 produced the highest levels of CTL activity by both routes (92% and 72% specific lysis by IV and SC respectively). Injection of 10 µg LPD/E7 particles induced intermediate levels of CTL activity in both cases, while 1 µg LPD/E7 induced significant CTL activity following IV administration only. Free E7 peptide showed no CTL induction by either route.

3. LPD/E7 Vaccination Protects Mice from HPV+ Tumor Formation

To determine if the induce immune response is adequate to provide protective immunity, mice were IV or SC vaccinated with either 20 µg E7 peptide in PBS, empty LPD, or LPD containing 20 µg of E7 peptide on day days 0 and 5. Untreated mice served as controls. Five days after the last vaccination, mice were SC challenged with $0.5 \times 10^6$ E7 expressing TC-1 cells. Mice that received LPD/E7 particles by either route failed to develop tumors, while control mice and mice that received LPD alone or free E7 peptide developed tumors within 12 days. (FIG. 19)

4. LPD/E7 Complexes can be Used to Eradicated Established HPV+ Tumors

To determine the potential of LPD/E7 complexes for use as a therapeutic strategy, subcutaneous tumors were established in C57BL6 mice by inoculation of 0.5×10⁶ TC-1 cells. On days 3 and 6 following inoculation, mice were injected IV or SC with LPD containing 10 µg of E7 peptide. To determine the importance of antigen delivery to the spleen in the generation of the observed immune responses, a group of mice that had their spleens surgically removed was included. Untreated mice and mice receiving empty LPD served as controls. All mice that received IV LPD/E7 peptide showed steady tumor shrinkage and complete regression within 2 weeks (FIG. 20). SC treatment also resulted in complete regression but with slower kinetics. As expected, empty LPD administration slowed tumor progression but failed to eradicate the tumors. The anti-tumor effect in asplenic mice depended on the route of administration. IV treatment showed tumor growth rates similar to those observed in mice treated with LPD alone, while SC delivery resulted in tumor regression. Untreated mice showed unimpeded tumor progression.

It has been shown that LPD administration to tumor bearing mice induces non-specific immune activation that can result in tumor regression (Whitmore, et al., *Gene Ther.* 6, 1867-1875 (1999); and Whitmore, et al., *Cancer Immunol Immunother.* 50, 503-514 (2001)). To confirm that tumor regression was due to an E7 specific response, ten days after the last treatment splenocytes were assayed for E7 specific tumor lytic activity. Consistent with previously published results, IV or SC injection of LPD without peptide induced a low level of apparent CTL activity while treatment with LPD/E7 resulted in the highest level of CTL activity in both cases (FIG. 21). Cells from untreated mice showed no lytic activity.

C. Discussion

Following IV administration, peptide containing LPD particles traffic to the spleen where they accumulate in the APC rich marginal zones (Basak, et al., *Blood* 99, 2869-2879 (2002); and McIlroy, et al., *Blood* 97, 3470-3477 (2001)). Flow cytometry identified the cells that take up LPD/E7 complexes as mainly CD11b and CD11c positive cells. Approximately 27% of all CD11c and 16% of CD11b positive cells show LPD uptake as soon as 12 h after injection and remained positive for at least 48 h. Over time these particles or the cells that have internalized them appear to traffic into the white pulp where immune activation can occur. These observations are consistent with recently published studies by Moron, et al. which suggest that CD11c+ CD11b+ cells in the marginal zone internalize VLPs and subsequently traffic to T-cell areas of the spleen (Moron, et al., *J Exp Med* 195, 1233-1245 (2002))

While only a small number of APCs presenting an antigen are needed to initiate an immune response, most tumor antigens represent self antigens and are inherently less immunogenic than virally encoded tumor antigens (Porgador, et al., *J Exp Med* 188, 1075-1082 (1998)). The ability of LPD particles to deliver antigen to a large number of APCs should be beneficial when delivering epitopes from these antigens.

Intravenous vaccination with as little as 1 µg of encapsulated peptide produces measurable antigen specific CTL activity and vaccination with 20 µg of peptide showed greater immune induction than other commonly used liposome/peptide delivery systems (SL liposomes). The level of immune induction is sufficient to protect mice against tumor formation and caused the complete regression of established tumors. IV Treatment of asplenic mice with LPD/E7 particles showed therapeutic effects similar to delivery of empty LPD particles to intact mice while the removal of the spleen showed no effect on SC administration. The differential effects of spleen removal are most likely due to the differences in the site of T cell activation depending on the route of administration. Following IV administration, T cells are activated in the spleen and its removal prevents effective priming. The fact that removal of the spleen does not completely remove the IV therapeutic effect could be the result of LPD uptake by APCs in other lymphatic tissues, such as lung or hepatic lymph nodes, or to the anti-tumor effect of LPD mediated by their ability to induce the production of $T_h1$ cytokines (IL-12, IFNγ, and TNFα) that possess direct anti-tumor activities (Whitmore, et al., *Gene Ther* 6, 1867-1875 (1999)). While the spleen plays a role in the production of these cytokines, a large amount of this production occurs in the liver and lung (Whitmore, et al. *Cancer Immunol Immunother* 50, 503-514 (2001)). However, when LPD/E7 is given SC the particles will drain into the local lymph nodes where successful priming can occur and removal of the spleen has no effect. The fact that IV vaccination consistently induced higher CTL activities than SC injection in combination with the observations in asplenic mice shows that antigen delivery to the spleen is important for the enhanced vaccination observed here.

These results seem to be in contrast with those obtained by others using liposome/peptide complexes for vaccination (Ignatius, et al. *Blood* 96, 3505-3513 (2000); and Ludewig, et al., *Vaccine* 19, 23-32 (2000)). In these studies, no immune response was observed upon IV administration. This discrepancy may be due to differences in liposome formulation used. LPD lipopolyplexes are more stable than non-polycation containing lipoplexes (Li, et al. *Gene Ther* 5, 930-937 (1998)). It has been reported that prolonged stability results in liposome accumulation in the spleen (Tam, et al. *Gene Ther* 7, 1867-1874 (2000)). In the absence of extended circulation, other formulations may be rapidly degraded and fail to deliver sufficient amounts of antigen to the spleen.

The use of LPD particles for vaccination has some significant advantages. The inclusion of plasmid DNA in the particles allows for great flexibility in vaccine design. While we used empty plasmid DNA to form our LPD particles, DNA encoding any gene of interest may be substituted. For example, while LPD has a built in adjuvant effect, this can be modified by using DNA encoding cytokines designed to skew the immune response in a particular direction, chemotactic factors, or costimulatory molecules.

The biophysical properties of the LPD formulation are also an advantage. Others have reported successful vaccination using liposome based peptide delivery strategies, however these systems are more complex and usually require higher doses of peptide or the inclusion of helper peptides or other stimulatory molecules (Ludewig, et al., *Vaccine* 19, 23-32 (2000)). From a pharmaceutical point of view, LPD particles can be lyophilized, stored for extended periods (at least 1 year), rehydrated, and used without any loss of efficacy (Li, et al. *J Pharm Sci* 89, 355-364. [pii] (2000)). These unique properties make large scale "off the shelf" applications possible for cancers with known immunodominant epitopes such as cervical cancer, prostate cancer and various her2/neu expressing cancers (Terasawa, et al. *Clin Cancer Res* 8, 41-53 (2002); Knutson, et al., *Clin Breast Cancer* 2, 73-79 (2001); Munger, et al., *Oncogene* 20, 7888-7898 (2001); and Zeng, G., *J Immunother* 24, 195-204 (2001)).

What is claimed is:

1. A method of inducing an immune response in a subject comprising administering to the subject an antigen/lipid complex comprising an antigen and a cationic lipid selected from the group consisting of 1,2-myristoyl-3-trimethylammonium propane (DMTAP), 1,2-distearoyl-3-trimethylammonium propane (DSTAP), 1,2-palmitoyl-3-trimethylammonium propane (DPTAP), 1,2-oleoyl-3- trimethylammonium propane (DOTAP), 1,2-dipalmitoyl-sn-glycero-3-ethylphosphocholine (DPEPC), 1,2-distearoyl-sn glycerol-3-ethylphosphocholine (DSEPC), 1,2-dimyristoyl-sn-glycero-3-ethylphophocholine (DMEPC), 1,2-dilauroyl-sn-glycero-3-ethylphosphocholine (DLEPC), 1,2-dioleoyl-sn-glycero-3-ethylphosphocholine (DOEPC), O,O'-dimyristyl-N-lysyl-aspartate (DMKE), O,O'-dimyristyl-N-lysyl-glutamate (DMKD), 2,3-dioleyloxy-N-[2 (sperminecarboxamido)ethyl]-N,N-dimethyl-1-propanaminium trifluoracetate (DOSPA), N-[1-(2,3-dioleyloxy)propyl]-n,n,n-trimethylammonium chloride (DOTMA) and combinations thereof to form an antigen/lipid complex to induce an immune response in the subject.

2. A method for stimulating an immune response to a tumor in a subject comprising administering to the subject the complex of claim 1 wherein said antigen is a tumor-associated antigen thereby stimulating an immune response to a tumor in the subject.

3. A method for inhibiting the growth of a tumor cell in a subject, said method comprising administering to a subject the complex of claim 1 wherein said antigen is a tumor-associated antigen, or a tumor-associated antigen modified to retain its antigenic activity but to eliminate its tumorigenic activity, thereby preventing or inhibiting the growth of a tumor cell in said subject.

4. The method of claim 3 wherein said tumor-associated antigen is an HPV 16 E7 protein or peptide.

5. The method of claim 4 wherein said HPV 16 E7 protein or peptide has been modified to retain its antigenic activity but to eliminate its tumorigenic activity.

* * * * *

UNITED STATES PATENT AND TRADEMARK OFFICE
CERTIFICATE OF CORRECTION

PATENT NO. : 7,303,881 B2
APPLICATION NO. : 11/121840
DATED : December 4, 2007
INVENTOR(S) : Leaf Huang It is certified that error appears in the above-identified patent and that said Letters Patent is hereby corrected as shown below:

Column 1, line approx. 40-41 reads "...on day 4, 6, 8, or 12, mice were s.c. injected with..." and should read -- on day 4, 6, 8, or 12; mice were s.c. injected with --.

Column 1, line approx. 58 reads "...were sc injected..." and should read -- were s.c. injected --.

Column 1, line approx. 60 reads "...were sc challenge with..." and should read -- were s.c. challenged with --.

Column 2, line approx. 28 reads "...immunized on day 0 and 14..." and should read -- immunized on days 0 and 14 --.

Column 2, line approx. 35 reads "...showed that, the line for..." and should read -- ...showed that the line for --.

Column 2, line approx. 57 reads "...immunized on day 0 and 14." and should read -- ...immunized on days 0 and 14. --.

Column 3, line 2 reads "On day 4 and 10,..." and should read -- On days 4 and 10, --.

Column 5, line approx. 20 reads "...chloride) (DOTMA)..." and should read -- chloride (DOTMA) --.

Column 11, line approx. 39-42 reads "...Coronoviridae (e.g. coronaviruses); Rhabdoviradae (e.g. vesicular stomstitis viruses, rabies viruses); Coronoviridae (e.g. coronaviruses); Rhabdoviradae (e.g. vesicular stomstitis viruses, rabies viruses);..." and should read -- Coronoviridae (e.g. coronaviruses); Rhabdoviradae (e.g. vesicular stomstitis viruses, rabies viruses); --.

Column 11, line approx. 50 reads "...Parvovirida..." and should read -- Parvoviridae --.

UNITED STATES PATENT AND TRADEMARK OFFICE
CERTIFICATE OF CORRECTION

PATENT NO. : 7,303,881 B2
APPLICATION NO. : 11/121840
DATED : December 4, 2007
INVENTOR(S) : Leaf Huang It is certified that error appears in the above-identified patent and that said Letters Patent is hereby corrected as shown below:

Column 12, line approx. 56 reads "...contents of which is hereby incorporated..." and should read -- contents of which are hereby incorporated --.

Column 13, line approx. 51 reads "...were prepared and LPD the percentage of cells that..." and should read -- were prepared and the percentage of cells that --.

Column 13, line approx. 56-57 reads "...to produces effective vaccination of those cells are capable of effectively presenting the..." and should read -- to produce effective vaccination of those cells that are capable of effectively presenting the --.

Column 14, line 5 reads "...up LPD particles (Please see data in...)" and should read -- up LPD particles (please see data in...) --.

Column 14, line approx. 67 reads "...648 (May 2003), a copy of which..." and should read -- 648 (May 2003)), a copy of which --.

Column 15, line approx. 10 reads "On days 4, 6, 8 or 12 following..." and should read -- On day 4, 6, 8 or 12 following --.

Column 15, line approx. 38 reads "...on day 0 and 5" and should read -- on days 0 and 5 --.

Column 15, line approx. 64 reads "...(Whitmore et al, 2001)." and should read -- (Whitmore et al., 2001). --.

Column 16, line 2 reads "...and injected them to animals and to see if..." and should read -- and injected them to animals to see if --.

Column 16, line approx. 15 reads "...(Whitmore et al, 2001)." and should read -- (Whitmore et al., 2001). --.

Column 16, line approx. 39 reads "...to the same extend,..." and should read -- to the same extent, --.

UNITED STATES PATENT AND TRADEMARK OFFICE
CERTIFICATE OF CORRECTION

| | | |
|---|---|---|
| PATENT NO. | : 7,303,881 B2 | |
| APPLICATION NO. | : 11/121840 | |
| DATED | : December 4, 2007 | |
| INVENTOR(S) | : Leaf Huang | |

It is certified that error appears in the above-identified patent and that said Letters Patent is hereby corrected as shown below:

Column 16, line approx. 49 reads "...and involves in tumor cell killing." and should read -- and involved in tumor cell killing. --.

Column 17, line approx. 17 reads "...is responsible for the some of the..." and should read -- is responsible for some of the --.

Column 17, line approx. 33 reads "...n, n, n, -trimetylammonium..." and should read -- n, n, n, -trimethylammonium --.

Column 18, line 2 reads "...were not due the possible detergent effect..." and should read -- were not due to the possible detergent effect --.

Column 18, line 35 reads "...the can prevent and treat tumors..." and should read -- that can prevent and treat tumors --.

Column 19, line approx. 11 reads "...(Madision, Wis.)." and should read -- (Madison, Wis.). --.

Column 19, line approx. 25 reads "...is unable to activated..." and should read -- is unable to activate --.

Column 19, line 29 reads "...Sac1-luc..." and should read -- SacI-luc --.

Column 19, line approx. 57 reads "...these date suggest..." and should read -- these data suggest --.

Column 20, line approx. 15 reads "...losses its oncogenic property..." and should read -- loses its oncogenic property --.

Column 20, line approx. 33 reads "...were purchased form..," and should read -- were purchased from --.

Column 20, line approx. 46-47 reads "...(Alabaster AL)." and should read -- (Alabaster, AL). --.

UNITED STATES PATENT AND TRADEMARK OFFICE
CERTIFICATE OF CORRECTION

| | | |
|---|---|---|
| PATENT NO. | : 7,303,881 B2 | |
| APPLICATION NO. | : 11/121840 | |
| DATED | : December 4, 2007 | |
| INVENTOR(S) | : Leaf Huang | |

It is certified that error appears in the above-identified patent and that said Letters Patent is hereby corrected as shown below:

Column 20, line approx. 54 reads "...St Louis Mo.) were..." and should read -- St. Louis, Mo.) were --.

Column 20, line approx. 67 reads "...according to Ignatius et al (29)." and should read -- according to Ignatius et al. (29). --.

Column 21, line approx. 32 reads "...Boston Mass.) for..." and should read -- Boston, Mass.) for --.

Column 21, line approx. 53 reads "...(San Diego Calif.)..." and should read -- (San Diego, Calif.) --.

Column 22, line approx. 34-35 reads "...particles induces significant..." and should read -- particles induce significant --.

Column 22, line approx. 54 reads "...determine if the induce immune response is..." and should read -- determine if the induced immune response is --.

Column 22, line approx. 57 reads "...on day days 0 and 5." and should read -- on days 0 and 5. --.

Column 22, line approx. 64 reads "...Used to Eradicated..." and should read -- Used to Eradicate --.

Column 23, line approx. 49 reads "...(2002))" and should read -- (2002)). --.

Column 27, line 2 (Claim 1) reads "...glycero-3-..." and should read -- glycerol-3- --.

Column 27, line 4 (Claim 1) reads "...glycero-3-ethylphophocholine..." and should read -- glycerol-3-ethylphosphocholine --.

UNITED STATES PATENT AND TRADEMARK OFFICE
CERTIFICATE OF CORRECTION

PATENT NO. : 7,303,881 B2
APPLICATION NO. : 11/121840
DATED : December 4, 2007
INVENTOR(S) : Leaf Huang It is certified that error appears in the above-identified patent and that said Letters Patent is hereby corrected as shown below:

Column 27, line 5 (Claim 1) reads "...glycero-3-..." and should read -- glycerol-3- --.

Column 27, line 6 (Claim 1) reads "...glycero-3-..." and should read -- glycerol-3- --.

Signed and Sealed this

First Day of September, 2009

David J. Kappos
*Director of the United States Patent and Trademark Office*

SEQUENCE LISTING

```
<160> NUMBER OF SEQ ID NOS: 5

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:overlapping
      PCR primer P1

<400> SEQUENCE: 1
ttgggatcca ccatgcatgg agatacacct ac                                    32

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence:overlapping
      PCR primer P2

<400> SEQUENCE: 2
cggaattcat tcttatggtt tctgagaacc gatggggcac aca                        43

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:overlapping
      PCR primer P3

<400> SEQUENCE: 3
gagacaactg gtctctactg ttat                                             24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:overlapping
      PCR primer P4

<400> SEQUENCE: 4
acagtagaga ccagttgtct ctgg                                             24

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence:human
      papillomavirus subtype 16 E7 oncogene
      tumor-associated antigen MHC class I restricted
      peptide

<400> SEQUENCE: 5

Arg Ala His Tyr Asn Ile Val Thr Phe
  1               5
```